US009383276B2

(12) United States Patent
Enoki et al.

(10) Patent No.: US 9,383,276 B2
(45) Date of Patent: Jul. 5, 2016

(54) EVALUATION METHOD AND EVALUATION SYSTEM FOR IMPACT FORCE OF LASER IRRADIATION DURING LASER PEENING AND LASER PEENING METHOD AND LASER PEENING SYSTEM

(75) Inventors: Manabu Enoki, Tokyo (JP); Akinori Matsui, Toyokawa (JP); Yuji Kobayashi, Toyokawa (JP)

(73) Assignee: SINTOKOGIO, LTD., Nagoya-shi, Aichi (JP)

( * ) Notice: Subject to any disclaimer, the term of this patent is extended or adjusted under 35 U.S.C. 154(b) by 687 days.

(21) Appl. No.: 13/813,960

(22) PCT Filed: Oct. 7, 2011

(86) PCT No.: PCT/JP2011/073763
§ 371 (c)(1),
(2), (4) Date: Feb. 4, 2013

(87) PCT Pub. No.: WO2012/056913
PCT Pub. Date: May 3, 2012

(65) Prior Publication Data
US 2013/0138363 A1    May 30, 2013

(30) Foreign Application Priority Data
Oct. 26, 2010    (JP) .................................. 2010-239283

(51) Int. Cl.
*G01L 5/00*    (2006.01)
*B23K 26/00*    (2014.01)
(Continued)

(52) U.S. Cl.
CPC ............ *G01L 5/0052* (2013.01); *B23K 26/0069* (2013.01); *B23K 26/03* (2013.01);
(Continued)

(58) Field of Classification Search
CPC ........ G01L 5/00; G01L 5/0047; G01L 5/0052;
G01N 29/045; G01N 29/14; G01N 29/2418;
B23K 26/00; B23K 26/03; B23K 26/0069;
C21D 10/00; C21D 10/005
See application file for complete search history.

(56) References Cited

U.S. PATENT DOCUMENTS 5,113,680 A    5/1992  Matsuura et al.
7,649,807 B2   1/2010  Ing
(Continued)

FOREIGN PATENT DOCUMENTS

CN        1261434 A      7/2000
CN      101392382 A      3/2009
(Continued)

OTHER PUBLICATIONS

Marti-Lopez et al., Optical Observation of Shock Waves and Cavitation Bubbles in High Intensity Laser-Induced Shock Processes, Jul. 1, 2009, Applied Optics, vol. 48, No. 19, pp. 3671-3680.*
(Continued)

*Primary Examiner* — Toan Le
(74) *Attorney, Agent, or Firm* — Drinker Biddle & Reath LLP

(57) ABSTRACT

A method of evaluating impact force input to a workpiece member with a laser irradiated in laser peening processing is provided. This evaluation method includes a signal acquiring step, an input function calculating step, and an evaluating step. In the signal acquiring step, a detected waveform is acquired. The detected waveform is output during the laser peening processing by an AE sensor that detects an elastic wave generated in the workpiece member. In the input function calculating step, an input function I(t) by laser irradiation is calculated. In the evaluating step, impact force is evaluated using the input function I(t) by the laser irradiation.

20 Claims, 22 Drawing Sheets

(51) Int. Cl.
*B23K 26/03* (2006.01)
*C21D 10/00* (2006.01)
*C21D 11/00* (2006.01)
*G01N 29/04* (2006.01)
*G01N 29/14* (2006.01)
*G01N 29/24* (2006.01)
*G01N 29/44* (2006.01)
*G06F 17/00* (2006.01)
*C21D 7/06* (2006.01)
*C21D 9/32* (2006.01)

(52) U.S. Cl.
CPC ............ *C21D 10/00* (2013.01); *C21D 10/005* (2013.01); *C21D 11/00* (2013.01); *G01N 29/045* (2013.01); *G01N 29/14* (2013.01); *G01N 29/2418* (2013.01); *G01N 29/4472* (2013.01); *G06F 17/00* (2013.01); *C21D 7/06* (2013.01); *C21D 9/32* (2013.01)

(56) References Cited

U.S. PATENT DOCUMENTS

2007/0075035 A1 4/2007 Repphun et al.
2007/0119824 A1 5/2007 Deaton, Jr. et al.
2009/0084767 A1 4/2009 Deaton, Jr. et al.

FOREIGN PATENT DOCUMENTS

| JP | 4-19071 | 1/1992 |
| JP | 08-15115 A | 1/1996 |
| JP | 2003-315171 | 11/2003 |
| JP | 2005-321376 A | 11/2005 |
| JP | 2008-509412 A | 3/2008 |
| WO | 2010/057661 | 5/2010 |

OTHER PUBLICATIONS

Chen et al., Shock-Wave Propagation and Cavitation Bubble Oscillation by Nd: YAG Laser Ablation of a Metal in Water, Jun. 1, 2004, Applied Optics, vol. 43, No. 16, pp. 3251-3257.*

D.J. Buttle et al., "Characterization of particle impact by quantitative acoustic emission," Wear, NL, Elsevier, vol. 137, No. 1, Apr. 1990, pp. 63-90.

S-K. Lee et al., "Identification of impact force on a thick plate based on the elastodynamic and higher-order time-frequency analysis," Proceedings of the Institution of Mechanical Engineers, Nov. 1, 2007, pp. 1249-1263, vol. 221, part C: Journal of Mechanical Engineering Science.

Manabu Enoki, "In situ damage monitoring during surface treatment of materials," Strength, Fracture and Complexity, XP009156763, 2011, pp. 53-60, vol. 7, No. 1.

A Sasoh et al., "Behavior of bubbles induced by the interaction of a laser pulse with a metal plate in water," Applied Physics A: Materials Science & Processing, Apr. 1, 2005, pp. 1497-1500, vol. 80, No. 7.

* cited by examiner (a)

(b)

(a)

(b)

(a)

(b)

(a)

(b)

EVALUATION METHOD AND EVALUATION SYSTEM FOR IMPACT FORCE OF LASER IRRADIATION DURING LASER PEENING AND LASER PEENING METHOD AND LASER PEENING SYSTEM

TECHNICAL FIELD

The present invention relates to an evaluation method and an evaluation system for impact force of laser irradiation during laser peening and a laser peening method and a laser peening system. More specifically, the present invention relates to a method of evaluating, using a result obtained by using an AE (Acoustic Emission) sensor, impact force input to a workpiece member (material) during laser peening and a laser peening method and a laser peening system for irradiating a laser on the basis of knowledge obtained by the evaluation method and an evaluation system.

BACKGROUND ART

Conventionally, shot peening intensity has been evaluated using an arc height value obtained by using an almen strip. However, in quality management of the present state, in some cases, the shot peening intensity is managed using a peak value and depth of residual stress rather than the arc height value. This residual stress can be measured by an X-ray diffraction method (see, for example, Patent Literature 1). However, although the residual stress on a material surface can be measured in a non-destructive manner by the X-ray diffraction method, since a measurement region of a workpiece member has to be shaved when it is desired to obtain a residual stress distribution on the inside, a residual stress distribution of an actual product cannot be measured without breaking the product. The X-ray diffraction method is measurement in a shielded space for convenience of use of an X ray and there is a limit in the size of the workpiece member. There are many limitations in an evaluation method because it is difficult to make an X ray incident on a complicated-shaped object such as a gear.

When shot peening intensity is evaluated using the almen strip, it is impossible to evaluate which degree of force is applied to the surface of the workpiece member during shot peening processing. Therefore, an apparatus that detect shot peening intensity during shot peening processing using an AE sensor is examined (see, for example, Patent Literature 2). The apparatus described in Patent Literature 2 includes the AE sensor arranged in a shot (shot media) peened area. The AE sensor converts an elastic wave generated by shot projection into a high-frequency electric signal (an AE waveform). This apparatus detects a media flow rate and peened intensity of the shot using a peak value and the number of times of waveform generation of a voltage waveform obtained by converting the AE waveform.

CITATION LIST

Patent Literature

Patent Literature 1: Japanese Patent Application Laid-Open Publication No. 2003-315171
Patent Literature 2: Japanese Patent Application Laid-Open Publication No. 04-19071

SUMMARY OF INVENTION

Technical Problem

However, in the shot peening, for example, several tens of thousands of shots collide with the workpiece member in one process (several tens of seconds). Places where the shots collide are random with respect to a machined surface. Further, there is fluctuation in particle diameters of the shot media. Therefore, it is likely that a measured AE waveform is different every time.

On the other hand, there is laser peening as a type of peening. A characteristic of the laser peening is reproducibility of output energy. Processing is considered to be surely performed because the laser peening has reproducibility. Laser peening is highly reliable processing. In the laser peening, a place to be irradiated is known in advance and there is the reproducibility. Therefore, it is expected that fluctuation in measured AE waveforms is small.

However, whereas a series of phenomena of the laser peening ends within 100 ns, time resolution of the AE sensor is several microseconds. Therefore, it is difficult to evaluate laser irradiation during the laser peening simply using the AE sensor.

Therefore, in this technical field, there is a demand for an evaluation method and an evaluation system for appropriately evaluating force applied to the surface of the workpiece member during the laser peening. There is also a demand for a laser peening method and a laser peening system for irradiating a laser on the basis of knowledge obtained by these evaluation methods.

Solution to Problem

The inventor obtained, as a result of earnestly examining a relation between the AE sensor and the laser peening, knowledge that it is possible to estimate a shock wave from a change in a material rather than measuring laser irradiation and a fast shock wave and succeeded in evaluating laser irradiation during the laser peening with the AE sensor.

An evaluation method according to an aspect of the present invention is a method of evaluating impact force input to a workpiece member with a laser irradiated in laser peening processing. This evaluation method includes a signal acquiring step, an input function calculating step, and an evaluating step. In the signal acquiring step, a detected waveform is acquired. The detected waveform is output during the laser peening processing by an AE sensor that detects an elastic wave generated in the workpiece member. In the input function calculating step, an input function I(t) by laser irradiation is calculated. When the detected waveform is represented as V(t), the input function by the laser irradiation is represented as I(t), a response function of the AE sensor is represented as S(t), a green function of the workpiece member is represented as G(t), and a convolutional integral is represented as *, $$V(t) = S(t) * G(t) * I(t) \quad (1)$$

is obtained. The input function I(t) by the laser irradiation is calculated on the basis of this first relational expression, the response function S(t) of the AE sensor acquired in advance, the green function G(t) of the workpiece member acquired in advance, and the detected waveform V(t) acquired in the signal acquiring step. In the evaluating step, impact force is evaluated using the input function I(t) by the laser irradiation.

Since a series of phenomena of the laser irradiation ends within 100 ns, it is unknown what kind of effect the laser irradiation has on a material. Time resolution of the AE sensor is several micro seconds, which is considerably slow compared with the laser irradiation. However, an effect of the laser peening is a change in the material. Therefore, an elastic wave from which the change in the material can be read is measured by the AE sensor. Input energy can be estimated from the elastic wave. Consequently, it is possible to appropriately evaluate force applied to the surface of the workpiece member during the laser peening.

In an embodiment, in the input function calculating step, the input function I(t) may be calculated using at least an AE waveform for one wavelength including a first peak amplitude value, which is an amplitude value of a peak detected first in the detected waveform acquired in the signal acquiring step. This is because the first peak amplitude value directly represents a phenomenon.

In an embodiment, in the input function calculating step, the input function I(t) may be calculated using, in the detected wave acquired in the signal acquiring step, an amplitude value of a second detected waveform detected after a first detected waveform having an amplitude value attenuated from the first peak amplitude value set as a maximum. The second detected waveform of the detected waveform indicates an impact due to collapse of cavitation bubbles generated after ablation. Therefore, it is possible to evaluate the impact due to the collapse of the cavitation bubbles by using the amplitude value of the second detected waveform.

In an embodiment, the second detected waveform may be detected after at least 100 μs from the detection of the first detected waveform.

In an embodiment, the input function calculating step may include an estimating step. In the estimating step, a function representing attenuation of a peak amplitude value of the detected waveform acquired in the signal acquiring step may be estimated or specified. In the input function calculating step, the input function I(t) by the laser irradiation may be calculated using the function estimated or specified by the estimating step and the peak amplitude value. With such a configuration, it is possible to calculate the input function I(t) using an amplitude value of a peak other than the first peak amplitude value.

In an embodiment, the response function S(t) of the AE sensor and the green function G(t) of the workpiece member may be acquired by calibration and a simulation performed using a finite element method. The response function S(t) of the AE sensor and the green function G(t) of the workpiece member can be acquired in advance by the calibration and the simulation.

In an embodiment, the calibration may be performed using data obtained by breaking a lead of a mechanical pencil. In an embodiment, in the simulation performed using the finite element method, the green function G(t) of the workpiece member may be obtained using data concerning the shape and the material of the workpiece member and simulative impact force.

In an embodiment, when a detected waveform for the purpose of calculation is represented as $V_{test}(t)$, an input function for the purpose of calculation by an AE source is represented as $I_{test}(t)$, and the convolutional integral is represented as *, the green function G(t) of the workpiece member may be acquired by a simulation using a second relational expression:

$$V_{test}(t)=G(t)*I_{test}(t) \quad (2)$$

In an embodiment, a detected waveform $V_e(t)$ obtained by breaking a lead, the green function G(t) of which is known, may be acquired using the AE sensor, a detected waveform $V_{cal}(t)$ for the purpose of calculation may be acquired using an input function $I_{cal}(t)$ in breaking the lead according to a third relational expression:

$$V_{cal}(t)=G(t)*I_{cal}(t) \quad (3)$$

and the response function S(t) of the AE sensor may be calculated using a fourth relational expression:

$$V_e(t)=S(t)*G(t)*I_{cal}(t) \quad (4)$$

the third relational expression, and the green function G(t) obtained by the simulation.

An evaluation system according to another aspect of the present invention is an evaluation system that evaluates impact force input to a workpiece member by a laser irradiated in laser peening processing. The evaluation system includes a signal acquiring unit, an input function calculating unit, and an evaluating unit. The signal acquiring unit acquires a detected waveform output during the laser peening processing by an AE sensor that detects an elastic wave generated in the workpiece member. When the detected waveform is represented as V(t), the input function by the laser irradiation is represented as I(t), a response function of the AE sensor is represented as S(t), a green function of the workpiece member is represented as G(t), and a convolutional integral is represented as *, the input function calculating unit calculates an input function I(t) by laser irradiation using a first relational expression:

$$V(t)=S(t)*G(t)*I(t) \quad (1)$$

and on the basis of the response function S(t) of the AE sensor acquired in advance, the green function G(t) of the workpiece member acquired in advance, and the detected waveform V(t) acquired by the signal acquiring unit. The evaluating unit evaluates impact force using the input function I(t) by the laser irradiation.

With this evaluation system, input energy can be estimated on the basis of data obtained by measuring an elastic wave, from which a change in a material can be read, with the AE sensor. Consequently, it is possible to appropriately evaluate force applied to the surface of the workpiece member during the laser peening.

In an embodiment, the input function calculating unit may calculate the input function I(t) using at least an AE waveform for one wavelength including a first peak amplitude value, which is an amplitude value of a peak detected first in the detected waveform acquired by the signal acquiring unit. This is because the first peak amplitude value directly represents a phenomenon.

In an embodiment, the input function calculating unit may calculate the input function I(t) using, in the detected waveform acquired by the signal acquiring unit, a second detected waveform detected after a first detected waveform having an amplitude value attenuated from the first peak amplitude value set as a maximum. The second detected waveform of the detected waveform indicates an impact due to collapse of cavitation bubbles generated after ablation. Therefore, it is possible to evaluate the impact due to the collapse of the cavitation bubbles by using the second detected waveform.

In an embodiment, the evaluation system may further include a laser source and an AE sensor. The laser source irradiates a laser on the workpiece member. The AE sensor is attached to the workpiece member and receives an elastic wave generated in the workpiece member and outputs a detected waveform. The laser source irradiates the laser on a place different from a place where the AE sensor is attached.

In an embodiment, the detected waveform output from the AE sensor may be a waveform continuously measured at a maximum sampling rate of 10 MHz.

In an embodiment, the evaluation system may further include an analyzing unit. The analyzing unit analyzes the detected waveform output from the AE sensor and calculates a parameter indicating a waveform characteristic. The signal acquiring unit may be connected to a recording medium and continuously record the detected waveform output from the AE sensor in the recording medium or continuously record the parameter output from the analyzing unit.

In an embodiment, the response function S(t) of the AE sensor and the green function G(t) of the workpiece member may be acquired by calibration or a simulation performed using a finite element method.

In an embodiment, when a detected waveform for the purpose of calculation is represented as $V_{test}(t)$, an input function for the purpose of calculation by an AE source is represented as $I_{test}(t)$, and the convolutional integral is represented as *, the input function calculating unit may acquire the green function G(t) of the workpiece member according to a simulation using a second relational expression:

$$V_{test}(t)=G(t)*I_{test}(t) \quad (2)$$

In an embodiment, the input function calculating unit may acquire a detected waveform $V_e(t)$ obtained by breaking a lead, the green function G(t) of which is known, using the AE sensor, acquire a detected waveform $V_{cal}(t)$ for the purpose of calculation using an input function $I_{cal}(t)$ in breaking the lead according to a third relational expression:

$$V_{cal}(t)=G(t)*I_{cal}(t) \quad (3)$$

and calculate the response function S(t) of the AE sensor using a fourth relational expression:

$$V_e(t)=S(t)*G(t)*I_{cal}(t) \quad (4)$$

the third relational expression, and the green function G(t) obtained by the simulation.

A laser peening method according to still another aspect of the present invention is a method of performing peening processing with a laser. The laser peening method includes a signal acquiring step and an adjusting step. In the signal acquiring step, a detected waveform output during the laser peening processing by an AE sensor that detects an elastic wave generated in a workpiece member is acquired. In the adjusting step, power density of the laser is adjusted using a first peak amplitude value, which is an amplitude value of a peak detected first in the detected waveform acquired in the signal acquiring step, and an amplitude value of a second detected waveform detected after a first detected waveform having an amplitude value attenuated from the first peak amplitude value set as a maximum.

In a laser peening method according to still another aspect of the present invention, power density of a laser is adjusted using amplitude values of a first detected waveform and a second detected waveform. In this way, the power density is adjusted using not only the first detected waveform indicating an impact of ablation but also the second detected waveform indicating an impact due to collapse of cavitation bubbles. Therefore, it is possible to realize desired peening.

In an embodiment, in the adjusting step, the power density may be adjusted to minimum power density in a saturated range. By adjusting the power density in this way, it is possible to realize desired peening with minimum power.

In an embodiment, the laser peening method may further include an input function calculating step. In the input function calculating step, when the detected waveform is represented as V(t), the input function by the laser irradiation is represented as I(t), a response function of the AE sensor is represented as S(t), a green function of the workpiece member is represented as G(t), and a convolutional integral is represented as *, the input function I(t) by the laser irradiation may be calculated using a first relational expression:

$$V(t)=S(t)*G(t)*I(t) \quad (1)$$

on the basis of the response function S(t) of the AE sensor acquired in advance, the green function G(t) of the workpiece member acquired in advance, and the detected waveform V(t) acquired in the signal acquiring step. In the adjusting step, the power density of the laser may be adjusted using the input function I(t) by the laser irradiation.

A laser peening method according to still another aspect of the present invention is a laser peening method of obtaining a shock wave by causing ablation by a laser in a liquid, generating cavitation bubbles by a pressure change that occurs in the liquid, and obtaining a shock wave due to collapse of the cavitation bubbles to obtain two cycles of peening action. With this method, it is possible to obtain two cycles of peening action with one cycle of laser irradiation.

A laser peening method according to still another aspect of the present invention is a method in which the ablation is caused in the liquid in order to obtain a shock wave due to cavitation bubbles, the liquid is water, a vector of a shock wave due to the ablation is changed by water confining the shock wave due to the ablation, not allowing the shock wave due to the ablation to be dispersed to the outside, and wavelength of the laser is 532 nm as a second harmonic of 1064 nm such that the laser is not attenuated in the water and the water does not cause ablation. With this method, it is possible to obtain two cycles of peening action with one cycle of laser irradiation.

A laser peening system according to still another aspect of the present invention is a system that performs peening processing with a laser. This evaluation system includes a signal acquiring unit and an adjusting unit. The signal acquiring unit acquires a detected waveform output during the laser peening processing with an AE sensor that detects an elastic wave generated in a workpiece member. The adjusting unit adjusts power density of the laser using a first peak amplitude value, which is an amplitude value of a peak detected first in the detected waveform acquired by the signal acquiring unit, and an amplitude value of a first peak of a second detected waveform detected after a first detected waveform having an amplitude value attenuated from the first peak amplitude value set as a maximum.

In a laser peening system according to still another aspect of the present invention, power density of a laser is adjusted using amplitude values of a first detected waveform and a second detected waveform. In this way, the power density is adjusted using not only the first detected waveform indicating an impact of ablation but also the second detected waveform indicating an impact due to collapse of cavitation bubbles. Therefore, it is possible to realize desired peening.

In an embodiment, the adjusting unit may adjust the power density to minimum power density in a saturated range. By adjusting the power density in this way, it is possible to realize desired peening with minimum power.

In an embodiment, the laser peening system may further include an input function calculating unit. When the detected waveform is represented as V(t), the input function by the laser irradiation is represented as I(t), a response function of the AE sensor is represented as S(t), a green function of the workpiece member is represented as G(t), and a convolutional integral is represented as *, the input function calculating unit may calculate the input function I(t) by the laser irradiation using a first relational expression:

$$V(t)=S(t)*G(t)*I(t) \quad (1)$$

on the basis of the response function S(t) of the AE sensor acquired in advance, the green function G(t) of the workpiece member acquired in advance, and the detected waveform V(t)

acquired by the signal acquiring unit. The adjusting unit may adjust the power density of the laser using the input function I(t) by the laser irradiation.

Advantageous Effects of Invention

As explained above, according to the various aspects and embodiments of the present invention, an evaluation method for appropriately evaluating a force applied to the surface of a workpiece member during laser peening and an evaluation system for the evaluation method are provided. A laser peening method and a laser peening system for irradiating a laser on the basis of knowledge obtained by the evaluation method and the evaluation system are provided.

DESCRIPTION OF EMBODIMENTS

Figure 1:
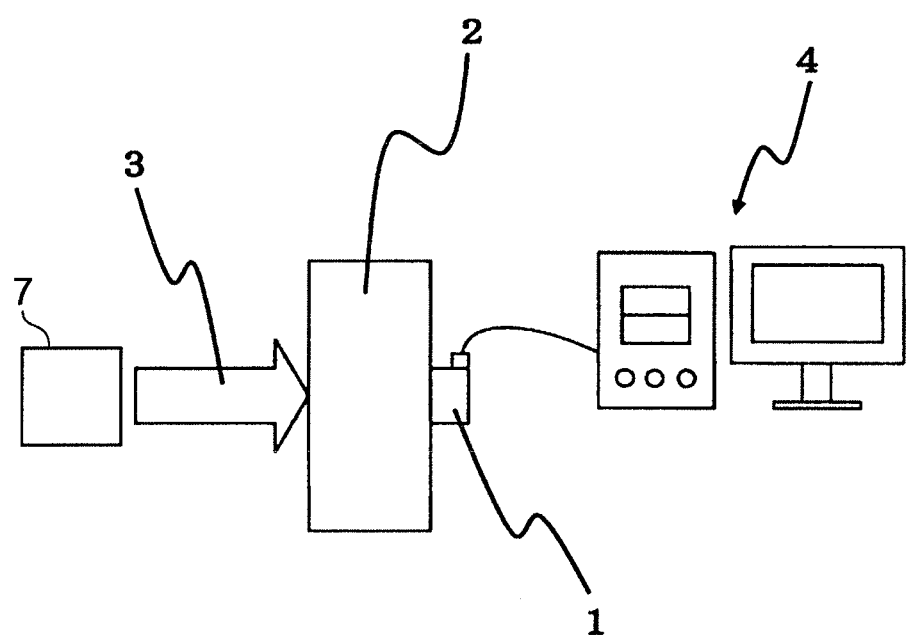
FIG. 1 is a schematic diagram in measuring an AE waveform during laser peening.

Various embodiments are explained in detail below with reference to the drawings. In the drawings, the same or equivalent components are denoted by the same reference numerals and signs.

Laser peening used in an embodiment confines, with water, plasma pressure due to ablation by a single-pulse laser and obtains a peening effect with a shock wave serving as reaction.

A series of phenomena of the laser peening ends within 100 ns. Therefore, it is unknown what kind of action the laser peening has on a material. Since time resolution of an AE sensor is several microseconds, the time resolution is considerably slow to measure a shock wave. However, the AE sensor picks up sound transmitted on the inside of metal. An effect of the laser peening is a change in the material. The change in the material appears in an elastic wave. Therefore, the elastic wave, from which the change in the material can be read, is measured rather than the shock wave having high speed and input energy is estimated. Specifically, impact force during the laser peening is measured and influence of the laser peening on the material is evaluated with impact force actually applied to the material, stress, or actually input energy rather than pulse energy of the laser.

The principle of the AE sensor is generally explained below. When a solid material is deformed or broken, distortion energy is consumed. Most of the consumed distortion energy is consumed for the deformation of the material and occurrence and development of a crack. However, the remaining energy is converted into sound, heat, and the like. A phenomenon in which sound is generated at this point is called AE. The phenomenon is defined as "a phenomenon in which distortion energy accumulated till then is released and an elastic wave is generated." A sensor that measures the elastic wave is an AE sensor. The AE sensor receives the elastic wave and outputs an AE waveform (a detected waveform). Distortion itself that causes the AE is referred to as AE source.

FIG. 1 is a schematic diagram in measuring an AE waveform during laser peening. First, an AE sensor 1 is attached to a workpiece member 2. In order to arrange the workpiece member 2 in water during the measurement, the AE sensor 1 is desirably an AE sensor having water resistance. For the attachment of the AE sensor 1, for example, an instant adhesive is used.

A laser 3 is irradiated from a laser source 7 on a place where the AE sensor 1 is not bonded (in FIG. 1, on the opposite side of the place where the sensor is bonded) to perform the laser peening. As the laser source 7, for example, a laser source that outputs a single-pulse laser is used. A peening effect is given to the workpiece member 2 by a shock wave generated during the laser peening. An elastic wave is generated by deformation of the workpiece member 2. The elastic wave is measured by the AE sensor 1. A signal of the elastic wave is acquired by a measuring instrument 4 functioning as elastic wave measuring means.

Figure 2:
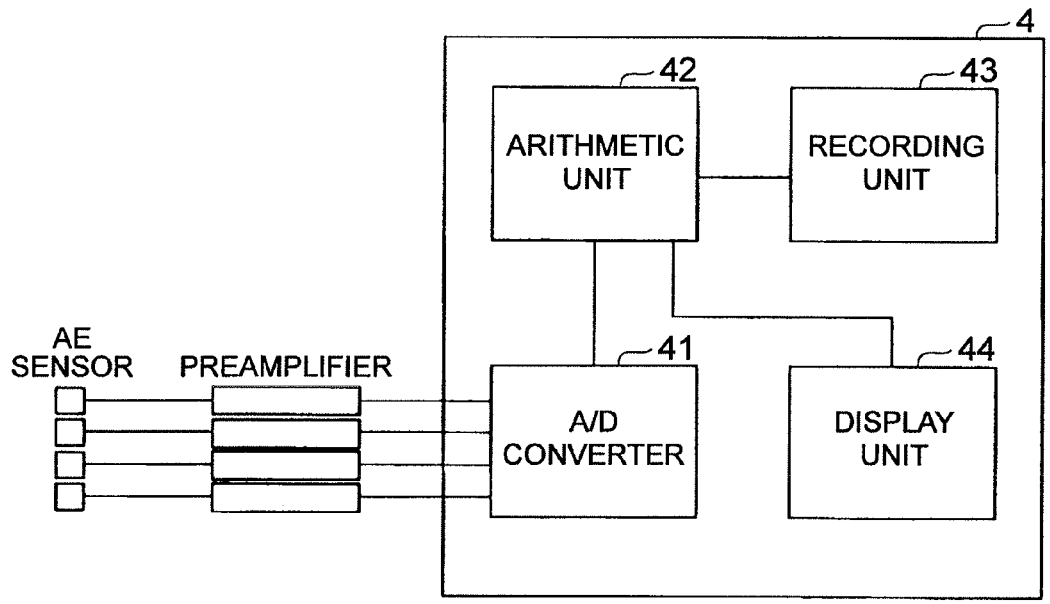
FIG. 2 is a configuration block diagram of hardware (a) and a functional block diagram of software (b) of a measuring instrument.
Figure 2:
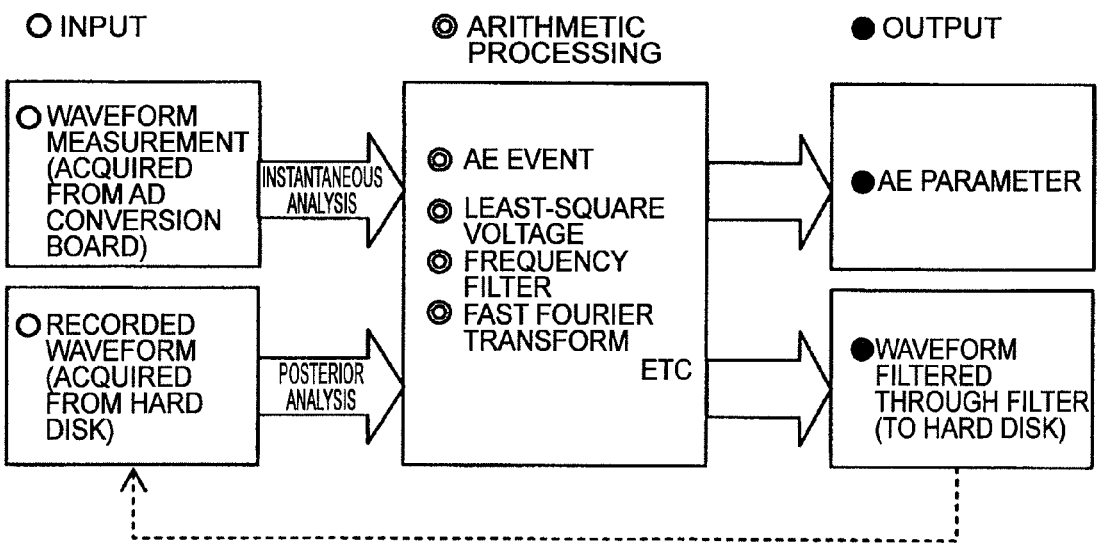

Details of the measuring instrument 4 are explained using FIG. 2. FIG. 2(a) is a block diagram of a hardware configuration of the measuring instrument 4 and FIG. 2(b) is a functional block diagram of software of the measuring instrument 4. The measuring instrument 4 is physically configured as a general computer system including a CPU (Central Processing Unit), main storage devices such as a ROM (Read Only Memory) and a RAM (Random Access Memory), an input device such as a keyboard, an output device such as a display, and an auxiliary storage device such as a hard disk. As shown in FIG. 2(a), the measuring instrument 4 includes an A/D converter 41, an arithmetic unit 42, a recording unit 43, and a display unit 44. One or plural AE sensors 1 are connected to the measuring instrument 4 via a preamplifier. The A/D converter is connected to the preamplifier and acquires a detected waveform (an AE waveform) output by the AE sensor 1. The A/D converter performs A/D conversion and outputs the detected waveform to the arithmetic unit 42. The arithmetic unit 42 controls the units of the measuring instrument 4 and analyze, edit, or record an AE waveform. The recording unit 43 is connected to the arithmetic unit 42 and records an output of the arithmetic unit 42. The display unit 44 is connected to the arithmetic unit 42 and displays the output of the arithmetic unit 42.

Figure 3:
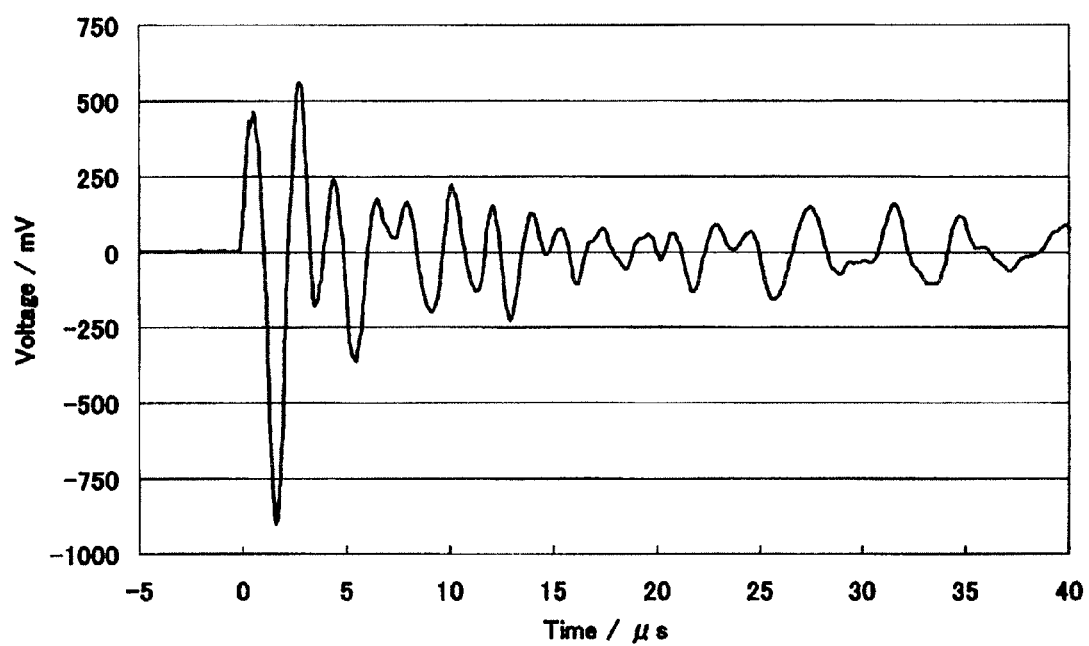
FIG. 3 is a graph showing an AE waveform obtained when a laser is irradiated once.

FIG. 2(b) is the software (a functional configuration) of the components of the measuring instrument 4 explained above. In input processing, the A/D converter 41 and the arithmetic unit 42 function. Specifically, the A/D converter 41 and the arithmetic unit 42 function as a signal acquiring unit. The signal acquiring unit acquires and records an AE waveform measured on-line (on a real time basis). For example, the signal acquiring unit continuously records the AE waveform according to a short-pulse laser continuously output from the laser source 7. An example of a measured AE waveform is shown in FIG. 3. The signal acquiring unit is configured to be capable of acquiring an AE waveform from a recording medium and acquiring an edited AE waveform. Therefore, the measuring instrument 4 is configured to be capable of performing an instantaneous analysis and a posterior analysis.

In arithmetic processing, the arithmetic unit 42 functions. The arithmetic unit 42 performs arithmetic processing of a frequency filter, fast Fourier transform, a least-square voltage, an AE event, and the like. Specifically, the arithmetic unit 42 functions as an analyzing unit that analyzes an AE waveform and calculates a parameter indicating a waveform characteristic. As the parameter, for example, maximum amplitude, a first peak amplitude value, an RMS (Root mean square) voltage value, rising time, a duration of an event, the number of times an amplitude value exceeds a threshold, an occurrence position of an event, a peak intensity frequency, and an average frequency, are used. The first peak amplitude value is an amplitude value of a peak detected first in a detected waveform. The rising time is time until the maximum amplitude is recorded after a voltage exceeds a threshold voltage. The duration of an event is time until the voltage finally falls below the threshold voltage after the voltage exceeds the threshold voltage. The analysis can be performed not only during the measurement but also after the measurement. The analysis can be performed under different conditions.

The arithmetic unit 42 has a function of calculating an input function I(t) by laser irradiation using an AE waveform and evaluating impact force. In other words, the arithmetic unit 42 functions as an input function calculating unit and an evaluating unit. This function is explained later.

In output processing, at least the arithmetic unit 42 functions. The arithmetic unit 42 outputs a calculated AE parameter and a detected waveform filtered through a frequency filter to the recording unit 43. A hard disk or a memory is used as the recording unit 43. The arithmetic unit 42 can output the AE parameter and the detected waveform to the display unit 44 and display the AE parameter and the detected waveform as a graph. For example, a display is used as the display unit 44.

Figure 4:
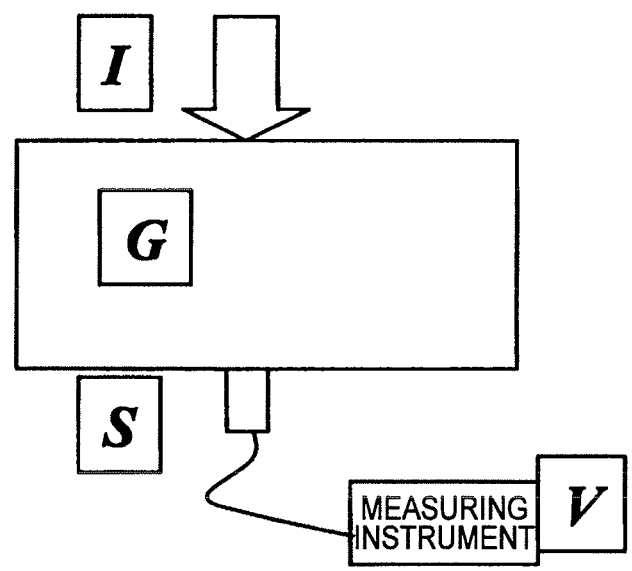
FIG. 4 is a conceptual diagram representing a relation among a detected waveform, a response function of a sensor, a green function of a medium sample, and an input function by an AE source.

Details of the arithmetic unit 42 functioning as the input function calculating unit and the evaluating unit are explained. The arithmetic unit 42 calculates an input function from an AE waveform using an inverse problem analyzing method. FIG. 4 is a conceptual diagram representing a relation among a detected waveform V(t), a response function S(t) of a sensor, a green function G(t) of a medium sample (a material, a workpiece member), and an input function I(t) by an AE source (distortion). A model shown in FIG. 4 indicates that the measured detected waveform V(t) is decided according to the input function I(t), the green function G(t), and the response function S(t). The measured AE waveform (detected waveform) V(t) is represented by a convolutional integral of the input function I(t) by the AE source, the green function G(t) of the medium sample (the material), and the response function S(t) of the sensor. This can be represented by the following expression (a first relational expression):

$$V(t)=S(t)*G(t)*I(t) \quad (1)$$

* indicates the convolutional integral.

As indicated by the expression, when the green function G(t) of the medium sample and the response function S(t) of the sensor are known in advance, the input function I(t) by the AE source can be calculated by performing an inverse convolutional integral from the detected waveform V(t). Impact force can be obtained on the basis of the input function I(t) by the AE source, i.e., an impact force function. In the following explanation, an example of methods of deriving the green function G(t) of the medium sample and the response function S(t) of the sensor is explained.

First, the method of deriving the green function G(t) is explained. The green function G(t) is derived on the basis of the shape, the mechanical characteristics, and the load of the workpiece member 2. For example, simulation software employing a finite element method is used. As such simulation software, LS-DYNA (registered trademark) (CAE software of Livermore Software Technology Corporation) is used. This software is explained as an example below.

Figure 5:
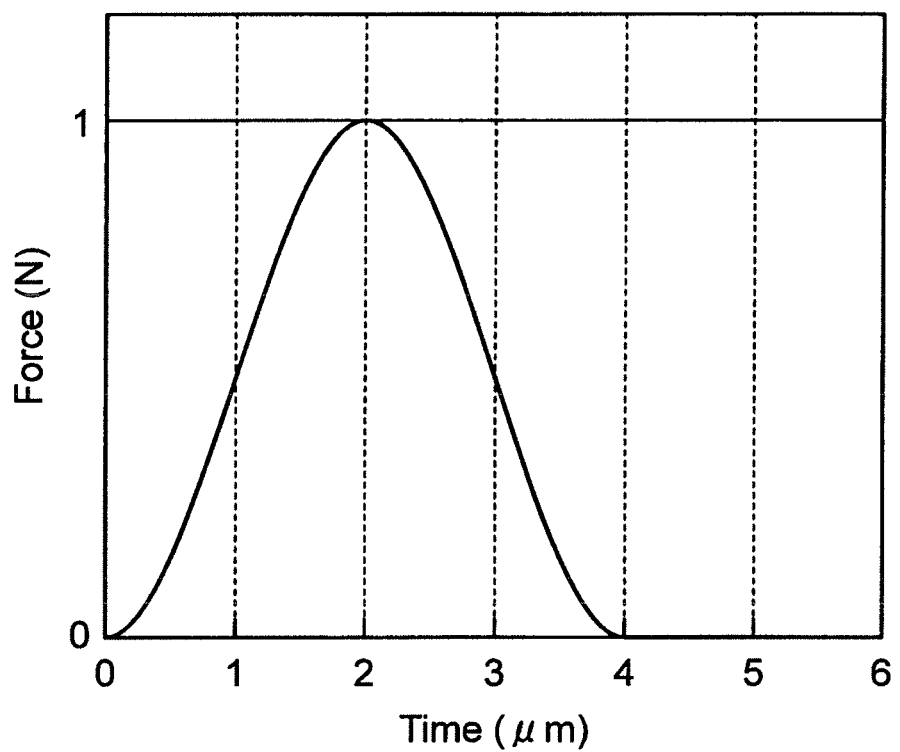
FIG. 5 is a graph showing a pseudo input function.

First, the shape of the workpiece member 2 is reproduced on the LS-DYNA. Subsequently, the mechanical characteristics and the simulative load of the workpiece member 2 are given to the LS-DYNA. For example, density, a Young's modulus, and a Poisson's ratio, which are the mechanical characteristics, of the workpiece member 2 are given. An input point (a point where force is actually applied), a direction in which the force is applied, and an output point (a position where the sensor is bonded) are given to the created shape of the workpiece member 2. A pseudo input signal (a pseudo input function) $I_{test}(t)$ of a load acting on the input point is given. For example, the pseudo input signal is a pseudo input signal shown in FIG. 5. In a graph shown in FIG. 5, the horizontal axis represents time and the vertical axis represents impact force. A detected waveform $V_{test}(t)$ at the output point can be obtained by performing simulation. $V_{test}(t)$ is represented by the following expression (a second relational expression):

$$V_{test}(t)=G(t)*I_{test}(t) \quad (2)$$

The green function G(t) is derived by performing the inverse convolutional integral of $I_{test}(t)$ using $V_{test}(t)$. For the inverse convolutional integral, software for numerical calculation MATLAB (registered trademark) (software of The MathWorks Inc.) can be used.

A method of deriving the sensor response function S(t) is explained. First, calibration is performed to measure an AE waveform $V_e(t)$. $V_e(t)$ is represented by the following expression (a fourth relational expression):

$$V_e(t)=S(t)*G(t)*I_{cal}(t) \quad (4)$$

Figure 6:
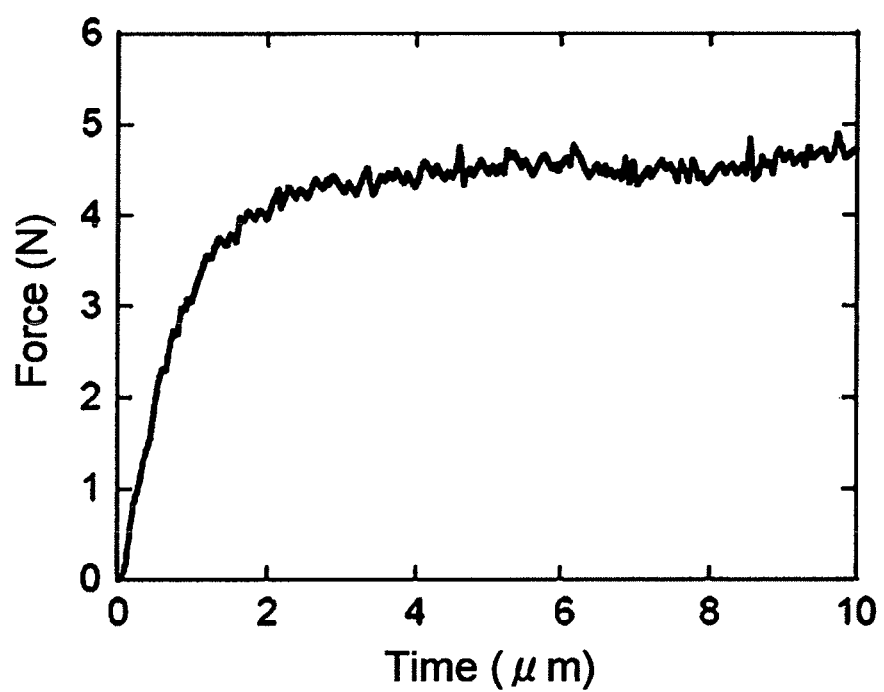
FIG. 6 is a graph showing an input function for press-breaking.

An input function $I_{cal}(t)$ is known. For example, an input function shown in FIG. 6 is used. In a graph shown in FIG. 6, the horizontal axis represents time and the vertical axis represents impact force.

The calibration is performed by breaking a predetermined shape and a lead of a material. For example, the calibration is performed using press-breaking of a lead of a mechanical pencil. The calibration performed using the lead of the mechanical pencil is explained below. This method is a method of breaking the lead of the mechanical pencil on a measurement target surface near the AE sensor, using an AE wave generated when the lead is broken as a sound source, and checking an amplitude value of a signal input to the AE sensor.

Figure 7:
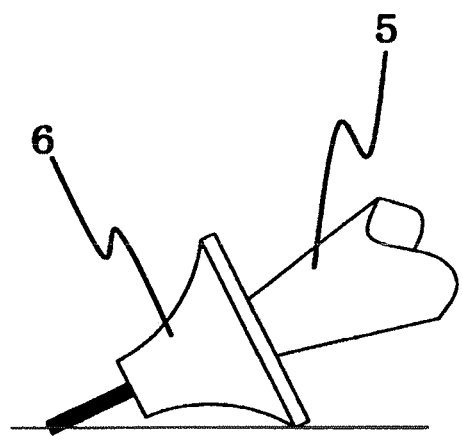
FIG. 7 is a diagram showing a jig used in a mechanical pencil lead press-breaking method.

In the mechanical pencil lead press-breaking method, the AE sensor is attached to the workpiece member 2 and a lead of a mechanical pencil 5 is press-broken near the AE sensor. Alternatively, the AE sensor may be attached to a material, the green function G(t) of which is known, and the lead of the mechanical pencil 5 may be press-broken near the AE sensor. For example, a lead having hardness of 2H and a diameter of 0.5 mm is pushed out 3 mm and press-broken at an angle of about 30 degrees (a jig 6 for this purpose is shown in FIG. 7). Stress released at this point is 5 N in 1 μs. The sensitivity of the measuring instrument 4 is adjusted and a physical amount of obtained data is estimated with reference to the stress. This mechanical pencil lead press-breaking method has a characteristic that verification can be performed in an actual measurement state. Other calibration methods such as a mutual calibration method and a contact method may be adopted.

On the other hand, the input signal (the input function) $I_{cal}(t)$ by press-breaking of a known lead is input to a model created on the LS-DYNA in the same manner as the method explained above and a simulation is performed, whereby a detected waveform $V_{cal}(t)$ of an output signal is obtained. $V_{cal}(t)$ is represented by the following expression (a third relational expression):

$$V_{cal}(t)=G(t)*I_{cal}(t) \quad (3)$$

The input signal $I_{cal}(t)$ of the fourth relational expression and the input signal $I_{cal}(t)$ of the third relational expression are the same. Specifically, $V_e(t)$ of the fourth relational expression is an experimental value and $V_{cal}(t)$ of the third relational expression is an estimated value. The sensor response function S(t) can be derived using the two detected waveforms $V_e(t)$ and $V_{cal}(t)$. Specifically, the sensor response function S(t) can be derived by performing the inverse convolutional integral of $V_{cal}(t)$ from $V_e(t)$. For the inverse convolutional integral, the software for numerical calculation MATLAB (registered trademark) (software of The MathWorks Inc.) can be used.

The green function G(t) and the response function S(t) of the sensor can be calculated in advance. The input function I(t) by the AE source can be calculated by performing the convolutional integral on the basis of the calculated green function G(t), the response function S(t) of the sensor, the AE waveform V(t) actually measured, and the first relational expression.

Figure 8:
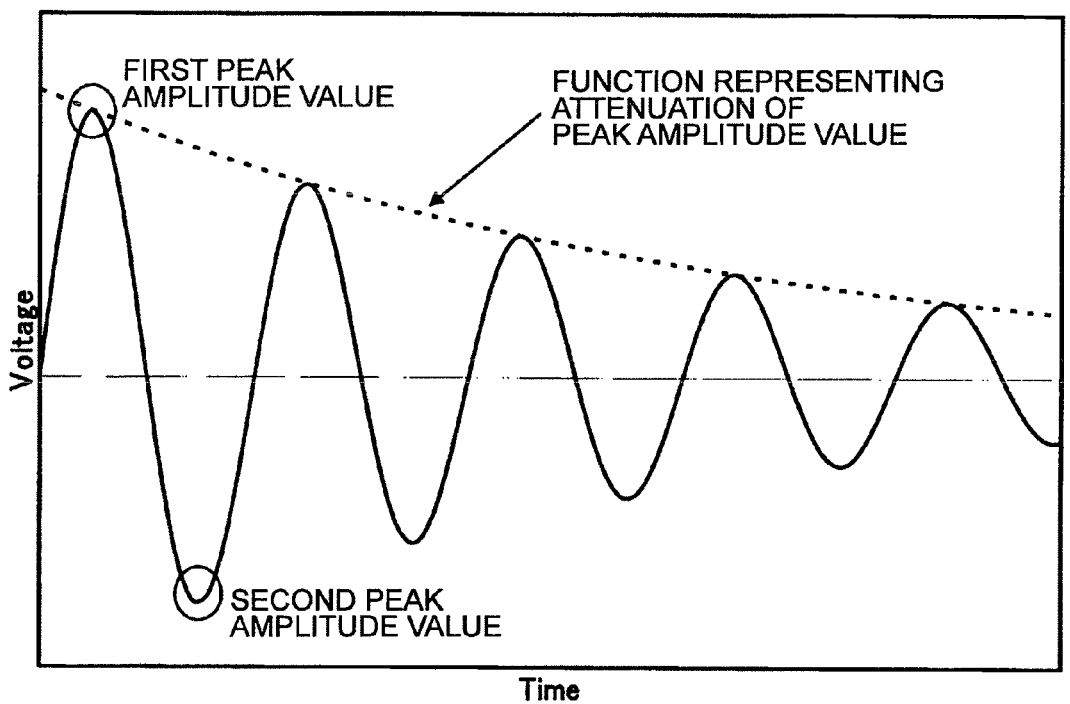
FIG. 8 is a graph showing a general waveform of a measured AE waveform.

The arithmetic unit 42 selects, in the AE waveform acquired from the AE sensor 1, a data range of the AE waveform used in the first relational expression as explained below. FIG. 8 is an example of the AE waveform. The arithmetic unit 42 selects the AE waveform for one wavelength including a first peak amplitude value, which is an amplitude value of a peak detected first in the AE waveform shown in FIG. 8.

Further, the arithmetic unit 42 may select, in the AE waveform acquired from the AE sensor 1, a data range of the AE waveform used in the first relational expression as explained below. For example, the arithmetic unit 42 may adopt a second detected waveform detected after a first detected waveform having an amplitude value attenuated from the first peak amplitude value set as a maximum. Concerning whether a detected waveform is the second detected waveform, for example, after an amplitude value of a peak of the first detected waveform decreases to be equal to or smaller than a predetermined value, when a detected waveform having an amplitude value of a peak equal to or larger than the predetermined value is measured, the detected waveform is determined as the second detected waveform. Alternatively, a detected waveform measured after a predetermined time elapses from occurrence time of a first peak of the first detected waveform may be determined as the second detected waveform. The data range of the AE waveform used in the first relational expression in the second detected waveform is selected by a method same as the method for the first detected waveform.

Further, the arithmetic unit 42 may estimate or specify, from a detected waveform, a function representing attenuation of a peak amplitude value and derive an amplitude value using the function. As long as the function representing the attenuation of the peak amplitude value is clarified, the amplitude value is not limited to the first peak amplitude value and any peak amplitude value may be used. Plural peak amplitude values may be used. The function representing the attenuation of the peak amplitude value can be estimated or specified from the AE waveform. For example, the function representing the attenuation of the peak amplitude value can be specified using fitting.

Figure 9:
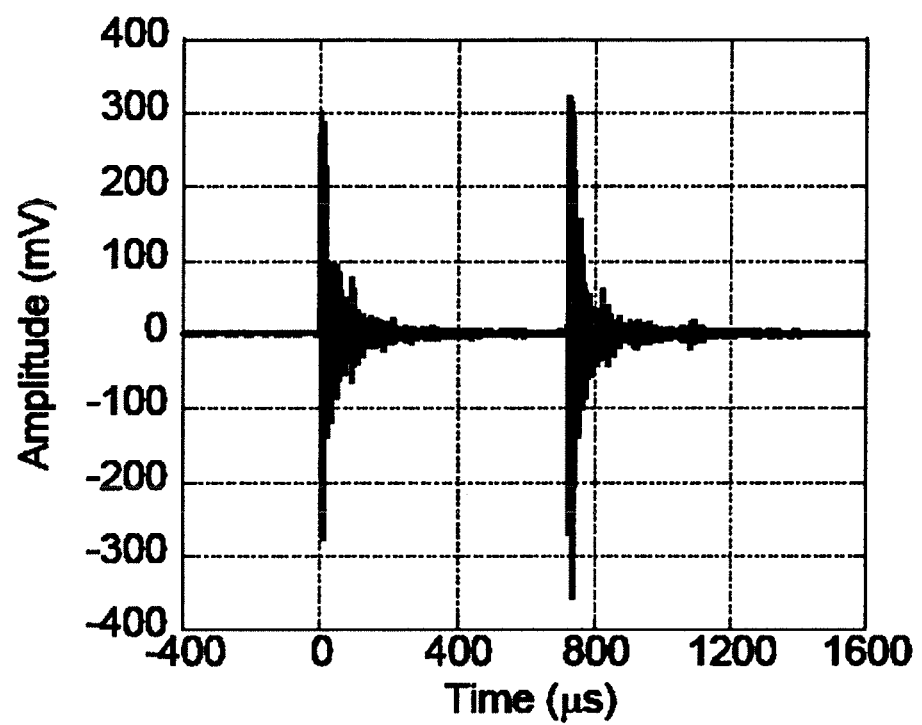
FIG. 9 is a first detected waveform and a second detected waveform of the AE waveform.
Figure 10:
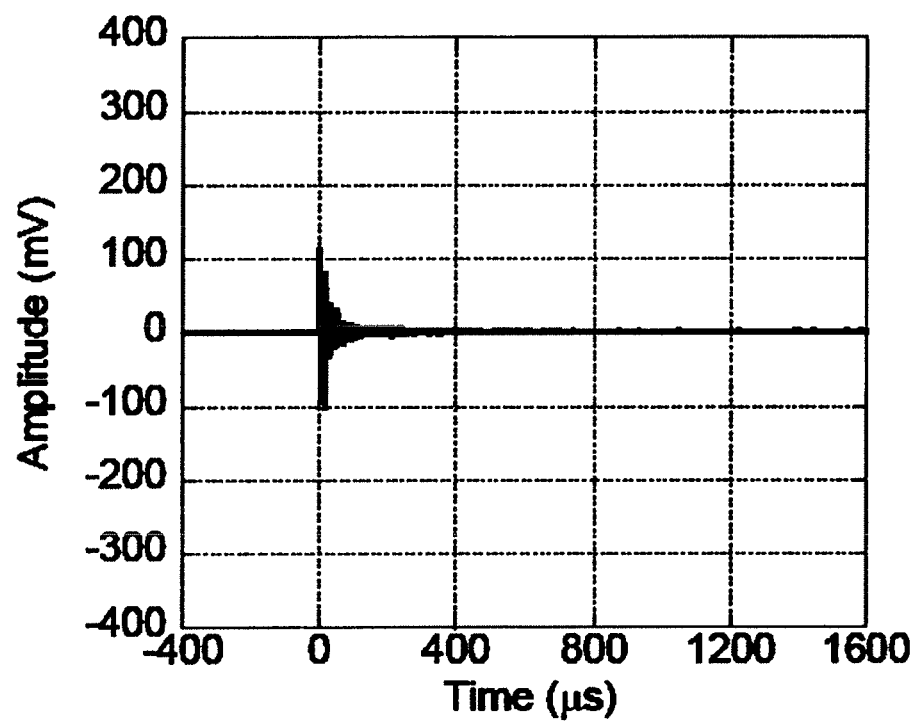
FIG. 10 is the first detected waveform of the AE waveform.

FIGS. 9 and 10 are examples of the AE waveform. An AE waveform shown in FIG. 9 is measured using water as a medium for trapping pressure generated during ablation. At this point, as the wavelength of the laser source 7, wavelength not causing ablation of the water (532 nm as a second harmonic of 1064 nm) is used. The wavelength of the laser source 7 can also be 1064 nm. On the other hand, an AE waveform shown in FIG. 10 is measured using glass as the medium for trapping pressure generated during ablation. When FIGS. 9 and 10 are compared, in FIG. 9, the second detected waveform detected after the first detected waveform having the amplitude value attenuated from the first peak amplitude value set as a maximum is observed. This second detected waveform is detected at least 100 μs after the first detected waveform is detected. In a detected waveform shown in FIG. 9, the first detected waveform indicates an impact due to ablation and the second detected waveform indicates an impact due to collapse of cavitation bubbles. In other words, impact force is evaluated concerning not only the first detected waveform but also the second detected waveform. This makes it possible to perform more accurate evaluation of laser peening processing.

Figure 11:
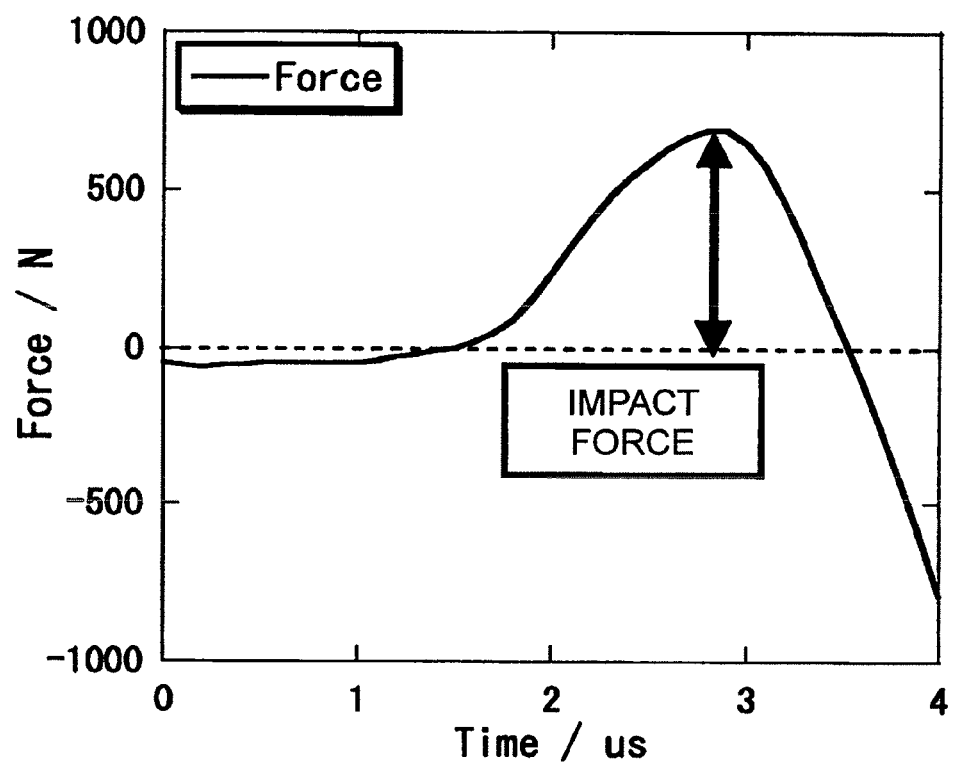
FIG. 11 is a graph showing impact force derived from the AE waveform shown in FIG. 8.

A method of evaluating impact force is explained. The arithmetic unit 42 evaluates impact force using the input function I(t) derived from the AE waveform V(t). FIG. 11 is a graph showing the input function I(t) derived from the AE waveform V(t) shown in FIG. 8. As shown in FIG. 11, the arithmetic unit 42 evaluates, for example, a maximum of the input function I(t) as impact force. In the explanation with reference to FIG. 11, impact force is evaluated using the first detected waveform. However, impact force can be evaluated in the same manner when the second detected waveform is used. Impact force may be comprehensively evaluated using the impact force evaluated using the first detected waveform and the impact force evaluated using the second detected waveform. For example, a sum of the impact forces may be calculated and evaluated.

An evaluation system includes the measuring instrument 4. The evaluation system includes the laser source 7, the AE sensor 1, and a preamplifier according to necessity. The recording unit 43 only has to be configured be capable of being referred to and written from the measuring instrument 4. Therefore, the evaluation system does not have to include the recording unit 43.

Figure 12:
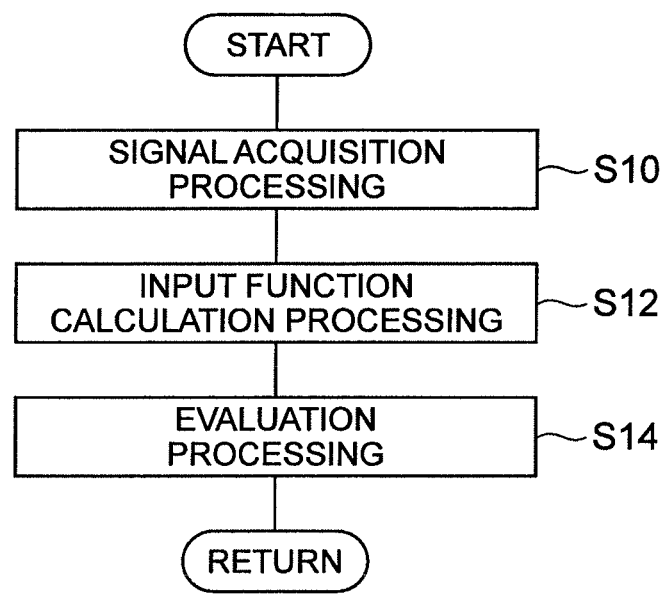
FIG. 12 is a flowchart showing the operation of an evaluation system.

The operation (an evaluation method) of the evaluation system is explained. FIG. 12 is a flowchart for explaining the operation of the evaluation system. As shown in FIG. 12, the evaluation system starts from signal acquisition processing (S10: a signal acquiring step). In the processing in S10, the A/D converter 41 and the arithmetic unit 42 acquire an AE waveform from the AE sensor 1 (on-line processing). When the AE waveform is acquired, the arithmetic unit 42 may estimate or specify a function representing attenuation of a peak amplitude value of the AE waveform (an estimating step). Alternatively, the arithmetic unit 42 acquires, referring to the recording unit 43, an AE waveform recorded in the past (off-line processing). When the processing in S10 ends, the processing shifts to input function calculation processing (S12: an input function calculating step).

In the processing in S12, the arithmetic unit 42 calculates, using the first relational expression, the input function I(t) by laser irradiation on the basis of the response function S(t) of the AE sensor acquired in advance, the green function G(t) of the workpiece member acquired in advance, and the detected waveform V(t) acquired in S10. When the processing in S12 ends, the processing shifts to evaluation processing (S14: an evaluating step).

In the processing in S14, the arithmetic unit 42 evaluates impact force using the input function I(t) calculated in S12. When the processing in S14 ends, control processing shown in FIG. 12 ends.

The evaluation system ends the operation of the evaluation system. It is possible to appropriately perform evaluation of the laser peening processing by executing the control processing shown in FIG. 12.

A laser peening method and a laser peening system for irradiating a laser using the evaluation system or on the basis of knowledge obtained using the evaluation system are explained.

Figure 13:
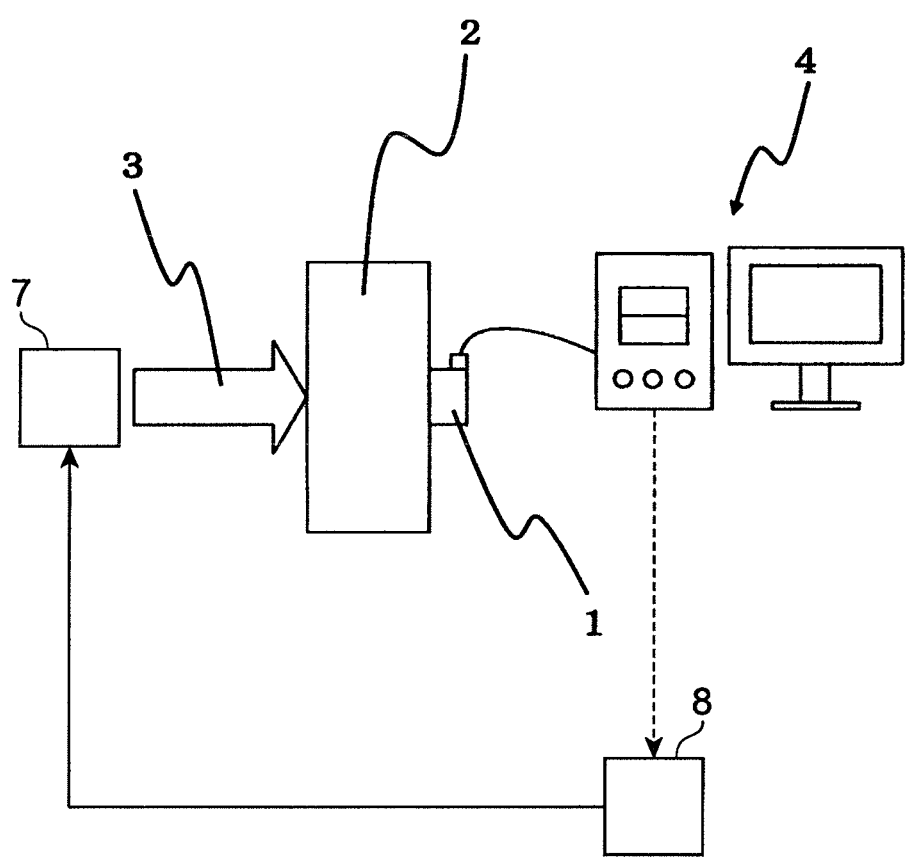
FIG. 13 is a conceptual diagram of a laser peening system.

FIG. 13 is a schematic diagram of the laser peening system. As shown in FIG. 13, the laser peening system includes the laser source 7, the AE sensor 1, the measuring instrument 4, and an adjusting unit 8. Functions of the laser source 7, the AE sensor 1, and the measuring instrument 4 are the same as those of the evaluation system explained above. The adjusting unit 8 adjusts an output of the laser source 7 on the basis of a measurement result of the measuring instrument 4. For example, the adjusting unit 8 adjusts power density (pulse energy) of the laser source 7.

The adjusting unit 8 adjusts, for example, power density of laser using the first peak amplitude value of the first detected waveform shown in FIG. 9 and an amplitude value of the second detected waveform. For example, the adjusting unit 8 adjusts the power density of the laser source 7 on the basis of a power density range in which the amplitude value of the second detected waveform approaches a maximum and a power density range in which the first peak amplitude value of the first detected wave approaches a maximum. Alternatively, the adjusting unit 8 may adjust the power density on the basis of the input function I(t) or the impact force evaluated by the measuring instrument 4. In other words, the adjusting unit 8 may adjust the power density on the basis of the input function I(t) or the impact force derived from the first detected waveform and the input function I(t) or the impact force derived from the second detected waveform. When water is used as the medium for trapping pressure generated during ablation and the wavelength of the laser source 7 is 532 nm as a second harmonic of 1064 nm, it is suitable to adjust the power density to minimum power density in a saturated range. More desirably, it is suitable to adjust the power density in a range of 3 to 8 $GW/cm^2$ including 5 $GW/cm^2$. It is possible to obtain a maximum peening effect with minimum power by adjusting the power density in this range. A method of trapping power generated during ablation can be either a method of setting the workpiece member 2 in water or a method of bathing the workpiece member 2 in flowing water. The method of bathing the workpiece member 2 in flowing water is a method of performing machining while spraying water on the workpiece member 2.

Figure 14:
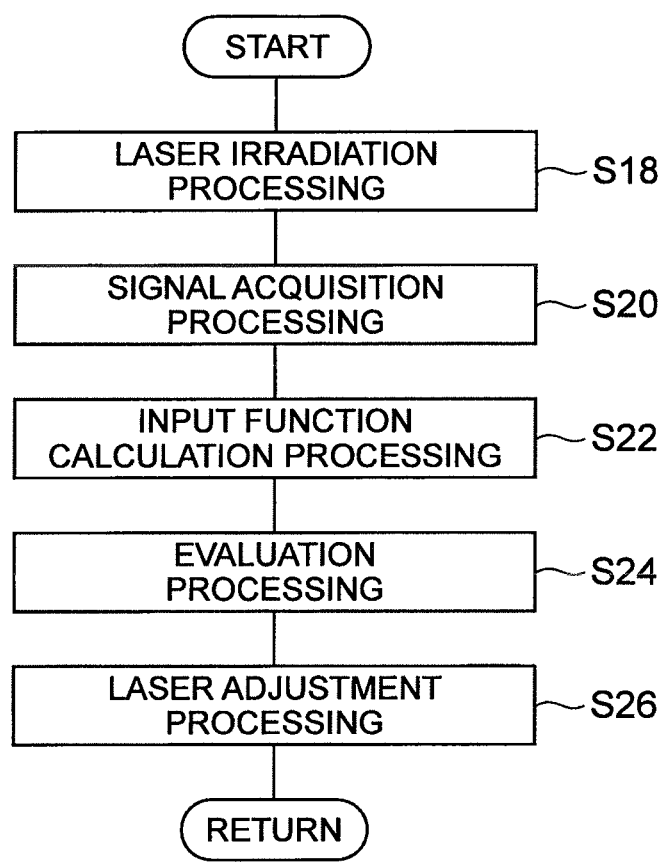
FIG. 14 is a flowchart for explaining the operation of the laser peening system.

The operation (a laser peening method) of the laser peening system is explained. FIG. 14 is a flowchart for explaining the operation of the laser peening system. As shown in FIG. 14, the laser peening system starts from laser irradiation processing (S18). In the processing in S18, a laser having power density adjusted by the adjusting unit 8 is irradiated from the laser source 7 to the workpiece member 2. When the processing in S18 ends, the processing shifts to signal acquisition processing (S20: a signal acquiring step). In the processing in S20, the A/D converter 41 and the arithmetic unit 42 acquire an AE waveform from the AE sensor 1 (on-line processing). When the AE waveform is acquired, the arithmetic unit 42 may estimate or specify a function representing attenuation of a peak amplitude value of the AE waveform (an estimating step). When the processing in S20 ends, the processing shifts to input function calculation processing (S22: an input function calculating step).

In the processing in S22, the arithmetic unit 42 calculates, using the first relational expression, the input function I(t) by laser irradiation on the basis of the response function S(t) of the AE sensor acquired in advance, the green function G(t) of the workpiece member acquired in advance, and the detected waveform V(t) acquired in S10. When the processing in S22 ends, the processing shifts to evaluation processing (S24: an evaluating step).

In the processing in S24, the arithmetic unit 42 evaluates impact force using the input function I(t) calculated in S22. When the processing in S24 ends, the processing shifts to laser adjustment processing (S26: an adjusting step).

In the processing in S26, the adjusting unit 8 adjusts power density using the impact force evaluated in S24. When the processing in S26 ends, the laser peening system ends control processing shown in FIG. 14.

the laser peening system ends the operation of the laser peening system. It is possible to feed back a measurement result and perform the laser peening processing by executing the control processing shown in FIG. 14. When the laser source 7 is adjusted from the AE waveform, the control processing shown in S22 and S24 does not have to be executed. When the laser source 7 is adjusted from the input function, the control processing shown in S24 does not have to be executed.

With the operation of the laser peening system explained above, it is possible to obtain a shock wave by causing ablation by a laser in liquid, generate cavitation bubbles due to a pressure change that occurs in the liquid, and obtain a shock wave due to collapse of the cavitation bubbles. In other words, it is possible to obtain two cycles of peening action with one cycle of laser irradiation. In order to obtain a shock wave due to cavitation bubbles, the ablation needs to be caused in the liquid. Water is used as the liquid. The water changes a vector (the direction of force) by confining the shock wave due to the ablation not to be diffused to the outside. The vector is the direction of force. As the wavelength of the laser, 532 nm as a second harmonic of 1064 nm is used to prevent the laser from being attenuated in the water and prevent ablation of the water. In this way, ablation is caused by irradiating a laser beam from the laser source on the surface of the workpiece member. When the peening processing is performed by an impact of the ablation, water is used as a medium for trapping pressure generated during ablation of the workpiece member 2 and the wavelength of the laser beam is set to 532 nm as a second harmonic of 1064 nm. Consequently, it is possible to cause cavitation bubbles after the ablation and obtain a peening effect with an impact due to collapse of the cavitation bubbles.

As explained above, with the evaluation system and the evaluation method according to the embodiment, it is possible to measure an elastic wave, from which a change in a material can be read, with the AE sensor and estimate input energy from the elastic wave. Consequently, it is possible to appropriately evaluate force applied to the surface of a workpiece member during laser peening. This makes it easy to grope for an optimum condition in the laser peening.

With the evaluation system and the evaluation method according to the embodiment, since the AE waveform for one wavelength including the first peak amplitude value directly representing a phenomenon is used, it is possible to perform appropriate evaluation.

With the evaluation system and the evaluation method according to the embodiment, it is possible to evaluate not only an impact due to ablation but also an impact due to collapse of cavitation bubbles by using the second detected waveform.

With the evaluation system and the evaluation method according to the embodiment, it is possible to calculate the input function I(t) using the AE waveform for one wavelength including the first peak amplitude value.

With the laser peening system and the laser peening method according to the embodiment, power density of a laser is adjusted using amplitude values of the first detected waveform and the second detected waveform. In this way, the power density is adjusted using not only the first detected waveform indicating an impact of ablation but also the second detected waveform indicating an impact due to collapse of cavitation bubbles. Therefore, it is possible to realize desired peening. Further, it is possible to two cycles of peening effect with one cycle of laser irradiation.

The embodiment explained above may be modified or may be applied to other systems and methods. For example, in the embodiment, the example in which the arithmetic unit 42 carries out both the calculation of the AE parameter and the calculation of the impact force (the green function and the response function) is explained. However, the present invention is not limited to this. For example, the arithmetic unit 42 may perform only the calculation of the AE parameter and another arithmetic unit may perform the calculation of the impact force. The other arithmetic unit may be included in the measuring instrument 4 or may be included in another computer.

EXAMPLES

Measurement of an AE waveform

An AE waveform was measured. As the workpiece member 2 on which a laser is irradiated, workpiece members having different thicknesses and of different materials were used. The workpiece member 2 had plane width of 35 mm×35 mm. Three kinds of workpiece members having thicknesses of 5 mm, 10 mm, and 20 mm were prepared. Two kinds of workpiece members of materials A7075 (Japanese Industrial Standards) and S50C (Japanese Industrial Standards) were prepared. In other words, six pieces of workpiece members 2 were prepared in total.

As the laser source 7, a Q switch Nd-YAG laser was used. Main specifications of the laser source 7 are shown in Table 1.

TABLE 1

| Maximum pulse energy | Wavelength | Pulse width | Spot area |
| --- | --- | --- | --- |
| 500 mJ | 532 nm | 7.5 ns | $1.09 \times 10^{-3}$ cm$^2$ |

Energy of the laser irradiated on the workpiece member 2 was adjusted by changing an angle of a polarization plate. Energy density of the laser was multiplied 23 times by a condenser lens. The laser was irradiated in the center of the surface of the workpiece member 2 fixed in the water by a jig. The laser 3 was irradiated five times per one condition.

One AE sensor 1 was attached to the center on the opposite side of the irradiated surface to measure AE during the laser irradiation. As the measuring instrument 4 that measured AE, an apparatus that could continuously measure signals at a sampling rate of 1 to 10 MHz at the maximum was used. In the example, the measuring instrument 4 continuously measured signals at a sampling rate of 10 MHz.

A waveform shown in FIG. 3 was confirmed every time the laser was irradiated once.

(Evaluation of Impact Force)

Figure 15:
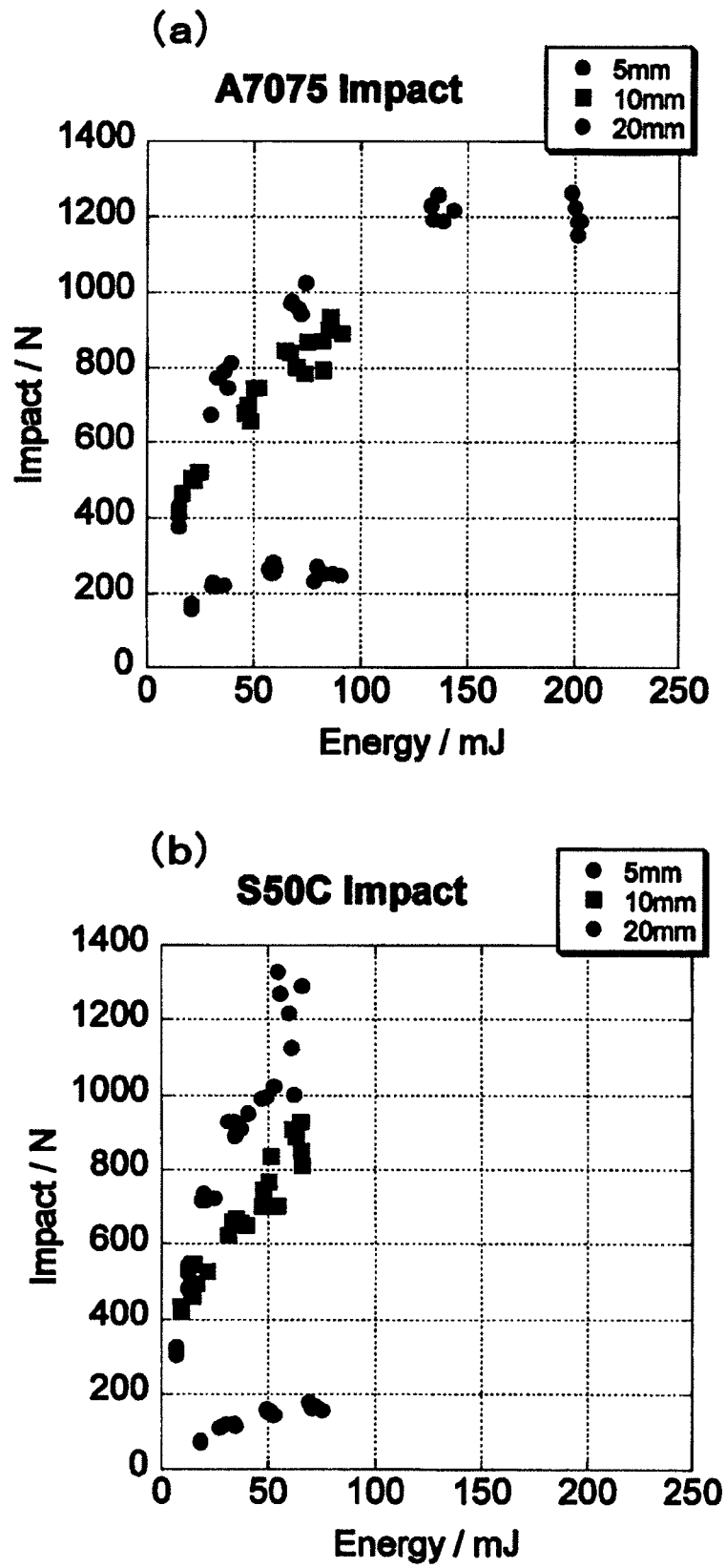
FIG. 15 is a graph in which impact force is plotted with respect to pulse energy. (a) is a case in which a material is A7075 and (b) is a case in which a material is S50C.

FIG. 15 is a graph in which the impact force obtained from the measured AE waveform as explained in the embodiment is plotted with respect to pulse energy. (a) is a graph in the case of A7075 and (b) is a graph in the case of S50C.

The impact force obtained this time was substantially equivalent to a value obtained by a VISAR (Velocity Interferometer System for Any Reflector) method, which is one of the impact wave measuring methods. Therefore, it can be said that the impact force obtained this time is a proper numerical value. As shown in FIG. 15, it is seen that a tendency of impact force calculated from an AE waveform is different depending on a difference in a material or thickness. Consequently, it was confirmed that the evaluation method and the evaluation system according to the present invention are effective.

When calibration is not used, although evaluation of an absolute value compared with the VISAR method cannot be performed, relative evaluation is possible.

(Adjustment of Power Density Based on an AE Waveform)

Figure 16:
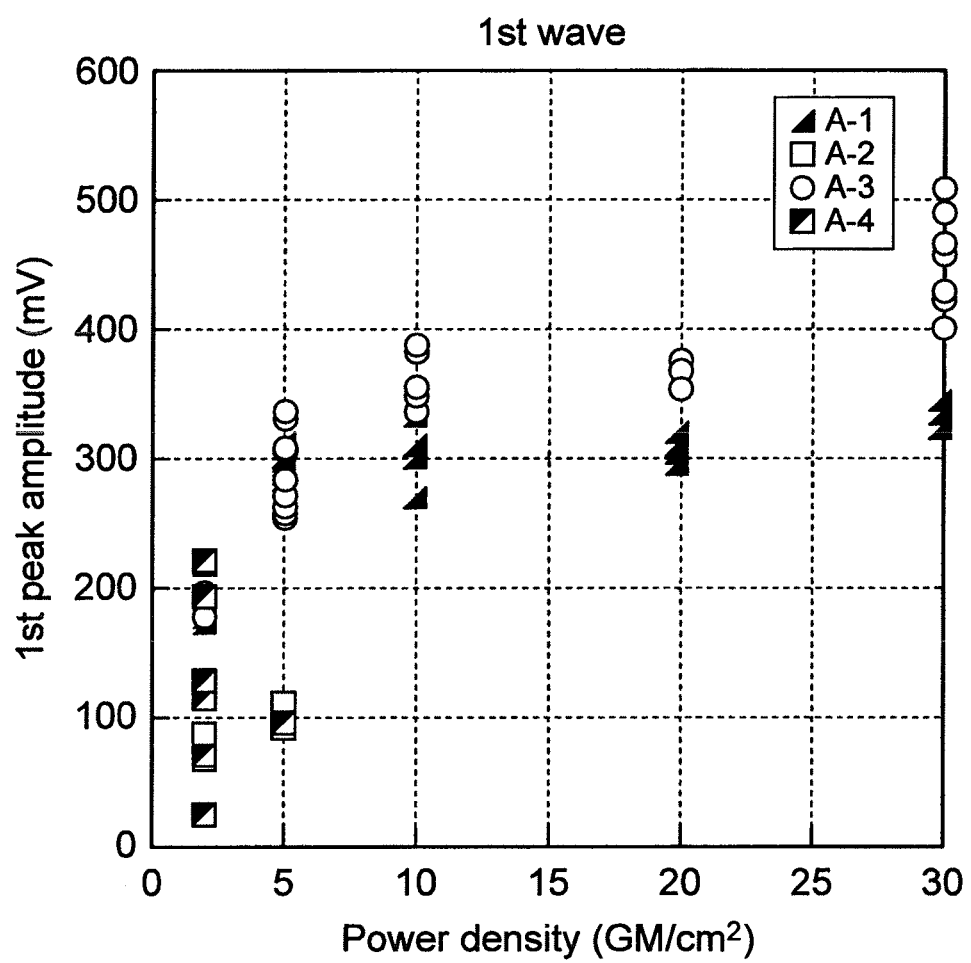
FIG. 16 is a graph in which a first peak amplitude value (intensity) of the first detected waveform is plotted with respect to power density.
Figure 17:
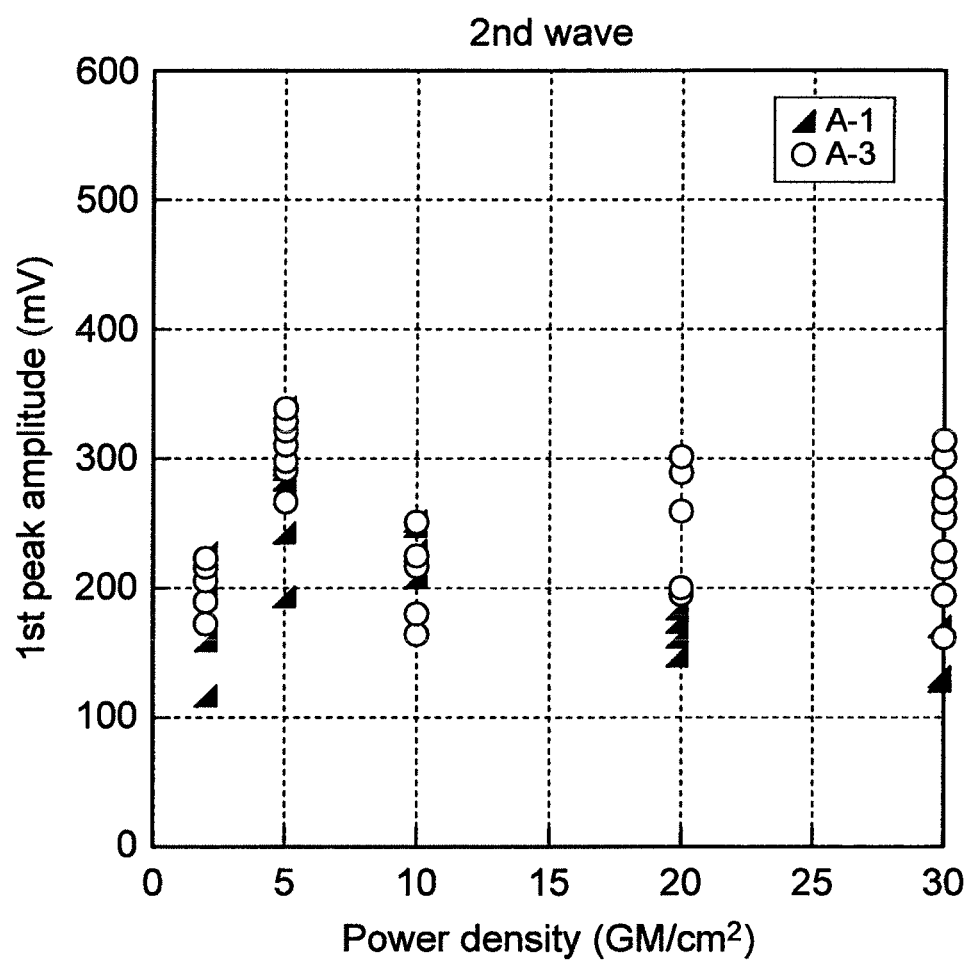
FIG. 17 is a graph in which a first peak amplitude value (intensity) of the second detected waveform is plotted with respect to power density.

FIG. 16 is a graph in which the first peak amplitude value (intensity) of the measured first detected waveform is plotted with respect to power density. A-1 is a case in which the laser is directly irradiated on the surface of the workpiece member, A-2 is a case in which glass is bonded to the surface of the workpiece member and the laser is irradiated, A-3 is a case in which a opaque layer (SUS 304 (Japanese Industrial Standards): thickness 15 μm) is bonded to the surface of the workpiece member and the laser is irradiated, and A-4 is a case in which the sacrificial layer and the glass are bonded to the workpiece member in this order and the laser is irradiated. FIG. 17 is a graph in which the amplitude value (intensity) of the peak detected first in the measured second detected waveform is plotted with respect to power density. A-1 is a case in which the laser is directly irradiated on the surface of the workpiece member and A-3 is a case in which a sacrificial layer (SUS 304: thickness 15 μm) is bonded to the surface of the workpiece member and the laser is irradiated. As shown in FIG. 16, the intensity of the first detected waveform was substantially fixed from the power density near 10 GW/cm². On the other hand, as shown in FIG. 17, the intensity of the second detected waveform was substantially fixed at the power density of about 5 GW/cm². Therefore, it was confirmed that it was suitable to adjust the power density to minimum power density in a saturated range. It was confirmed that, desirably, it is suitable to adjust the power density in a range of 3 to 8 GW/cm² including 5 GW/cm².

(Adjustment of Power Density Based on Impact Force)

Figure 18:
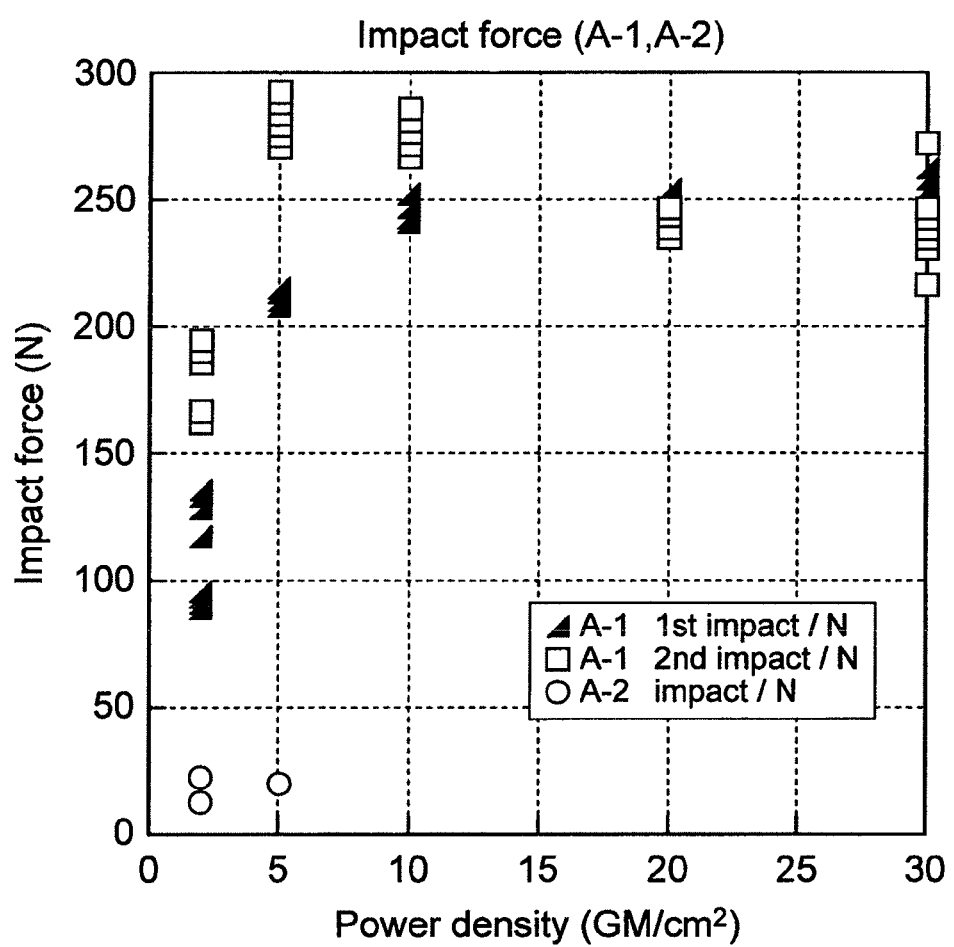
FIG. 18 is a graph in which impact force is plotted with respect to power density.
Figure 19:
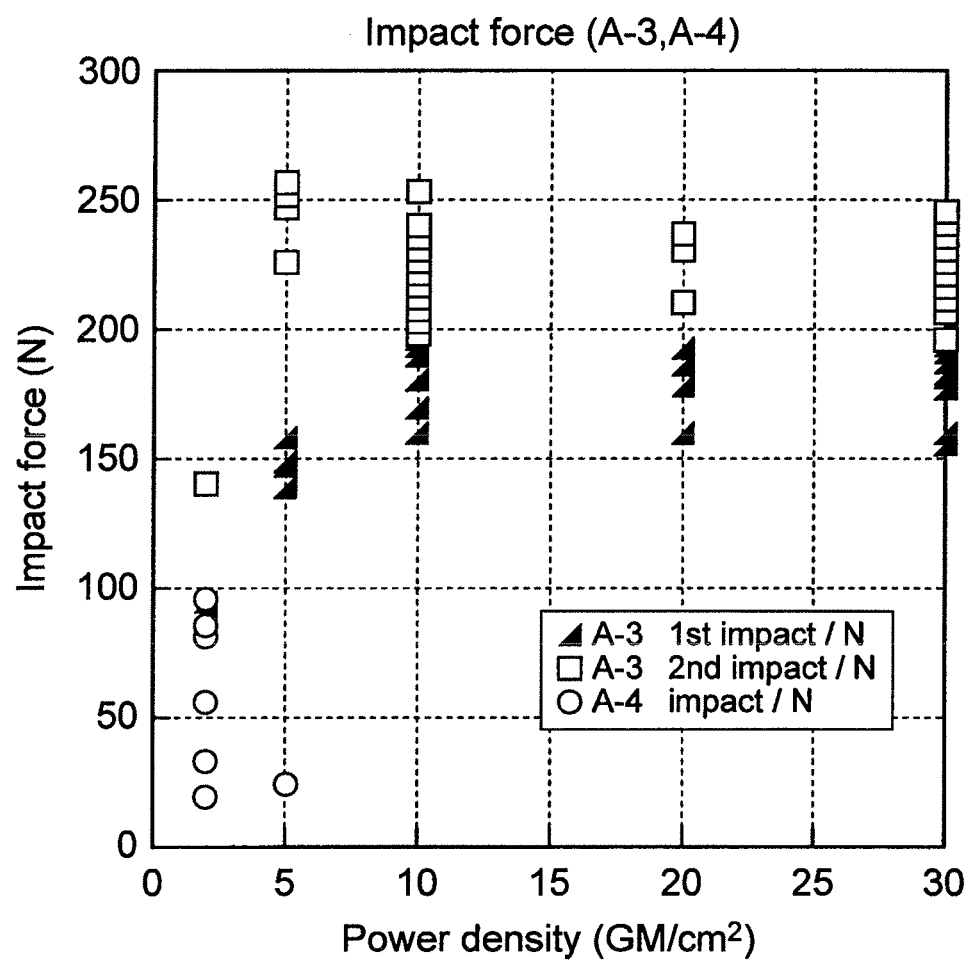
FIG. 19 is a graph in which impact force is plotted with respect to power density.

FIG. 18 is a graph in which impact force estimated from the AE waveform is plotted with respect to power density. A-1 is a case in which the laser is directly irradiated on the surface of the workpiece member. 1st impact indicates impact force estimated from the first detected waveform and 2nd impact indicates impact force estimated from the second detected waveform. A-2 is impact force in a case in which glass is bonded to the surface of the workpiece member and the laser is irradiated. FIG. 19 is a graph in which impact force estimated from the AE waveform is plotted with respect to power density. A-3 is a case in which a opaque layer (SUS304: thickness 15 μm) is bonded to the surface of the workpiece member and the laser is irradiated. 1st impact indicates impact force estimated from the first detected waveform and 2nd impact indicates impact force estimated from the second detected waveform. A-4 is a case in which the opaque layer and the glass are bonded to the workpiece member in this order and the laser is irradiated. As shown in FIGS. 18 and 19, even when the power density was evaluated using the impact force, it was confirmed that it was suitable to adjust the power density to minimum power density in a saturated range.

(Time Interval Between the First Detected Waveform and the Second Detected Waveform)

Figure 20:
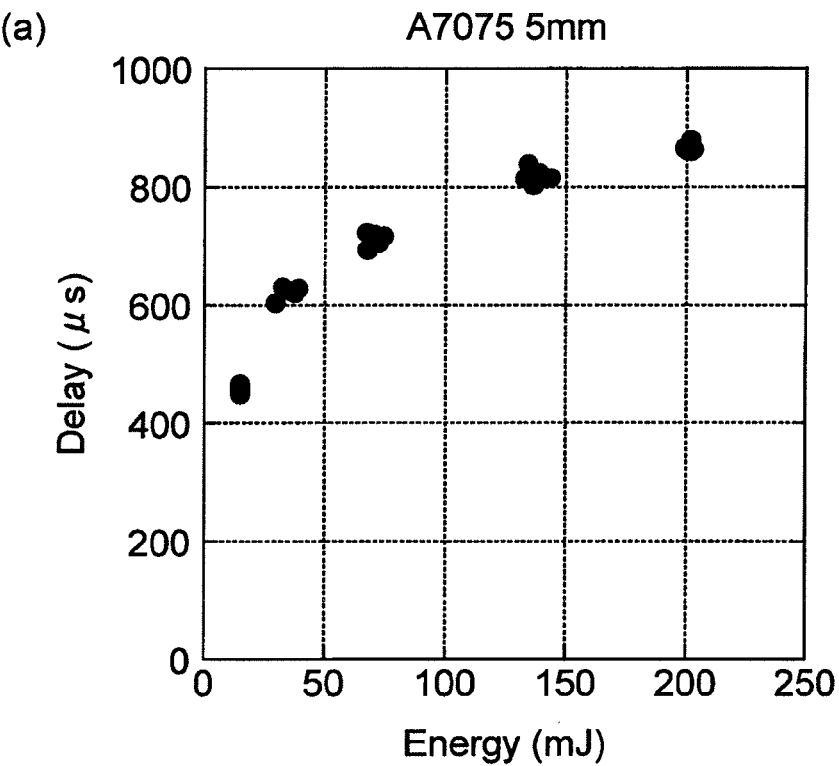
FIG. 20 is a graph in which a time interval between the first detected waveform and the second detected waveform is plotted with respect to pulse energy. (a) is a case in which a material is A7075 and (b) is a case in which a material is S50C.
Figure 20:
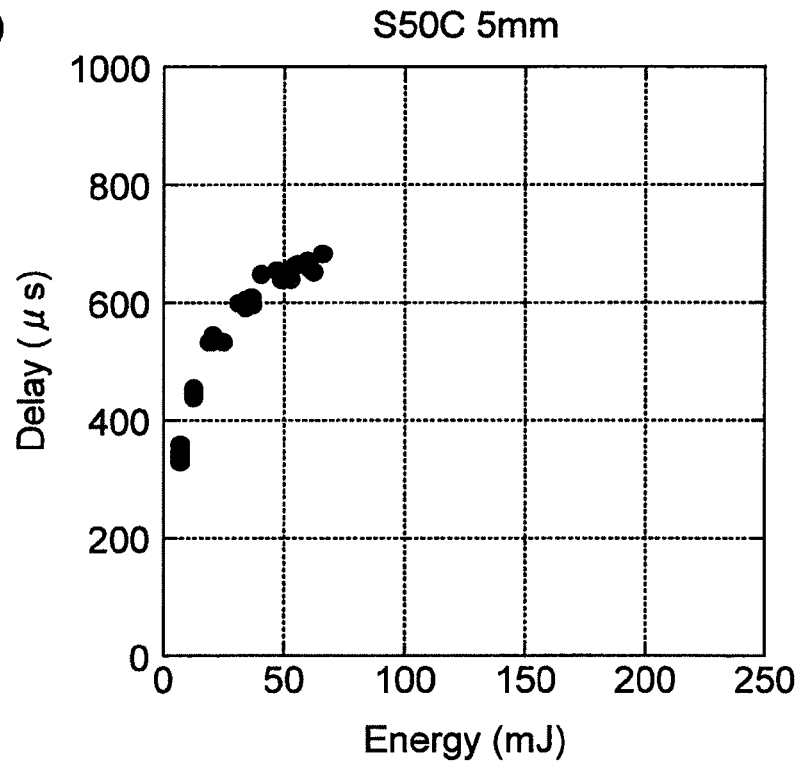
Figure 21:
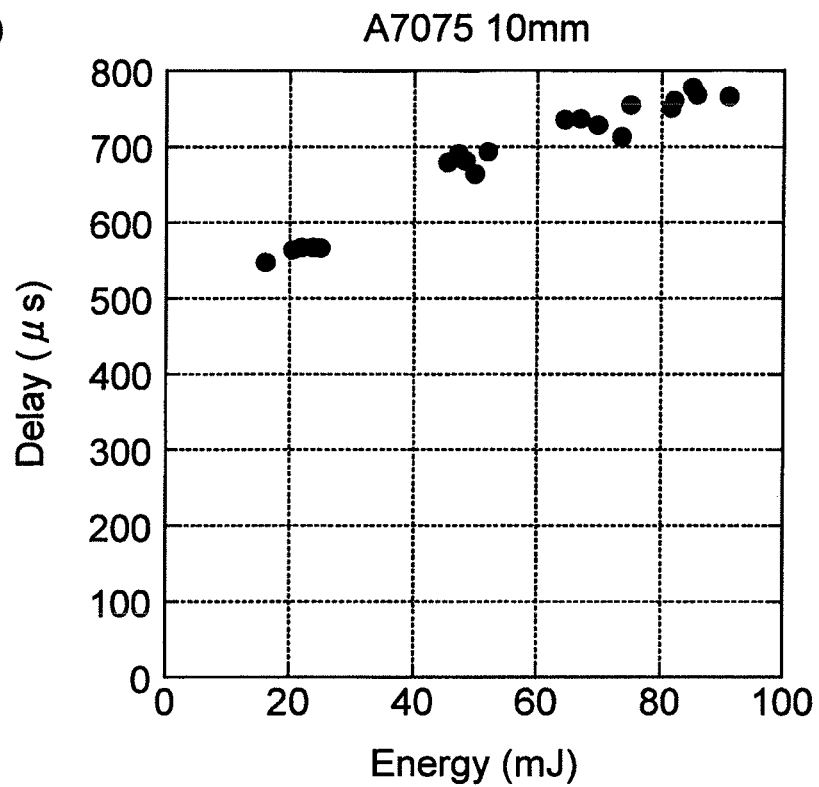
FIG. 21 is a graph in which a time interval between the first detected waveform and the second detected waveform is plotted with respect to pulse energy. (a) is a case in which a material is A7075 and (b) is a case in which a material is S50C.
Figure 21:
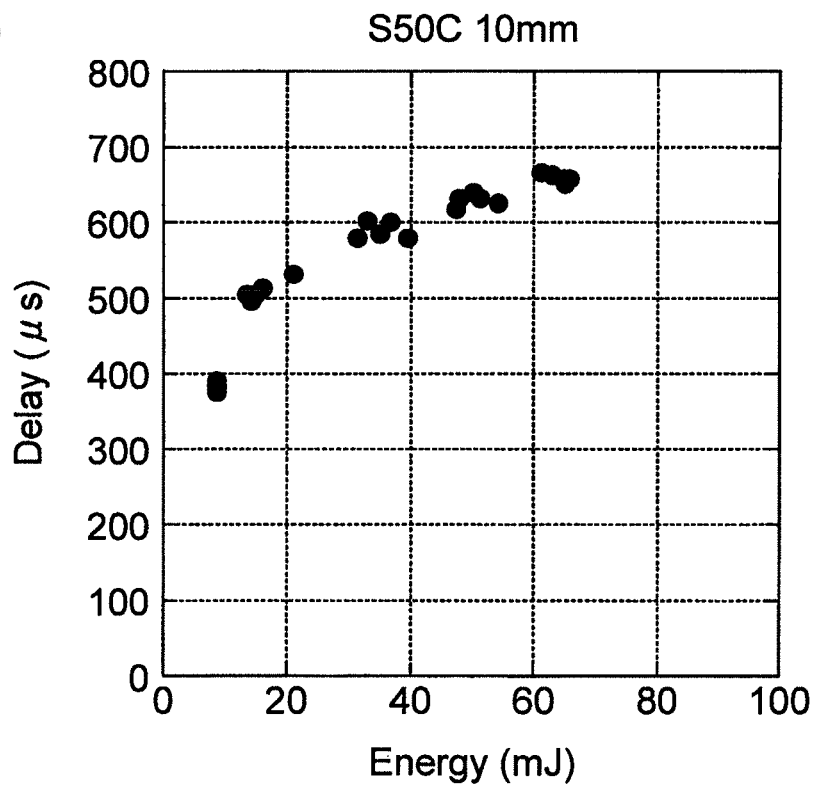
Figure 22:
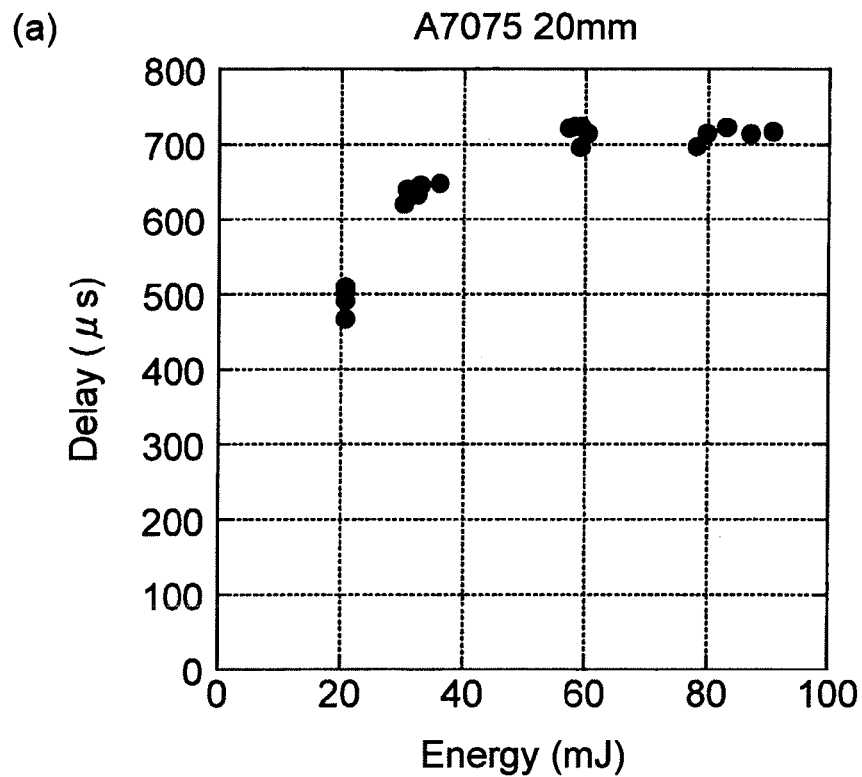
FIG. 22 is a graph in which a time interval between the first detected waveform and the second detected waveform is plotted with respect to pulse energy. (a) is a case in which a material is A7075 and (b) is a case in which a material is S50C.
Figure 22:
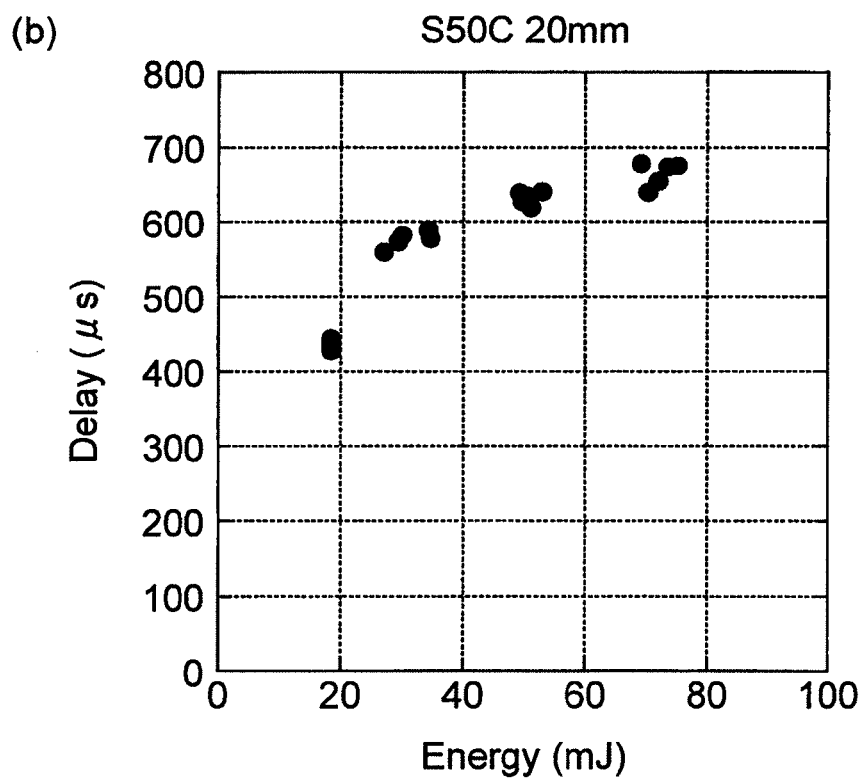

FIGS. 20, 21, and 22 are graphs in which a time interval between the first detected waveform and the second detected waveform is plotted with respect to pulse energy. (a) is a graph in the case of A7075 and (b) is a graph in the case of S50C. FIG. 20 is a graph in a case in which the thickness of a sample is 5 mm. FIG. 21 is a graph in a case in which the thickness of a sample is 10 mm. FIG. 22 is a graph in a case in which the thickness of a sample is 20 mm. As shown in FIGS. 20 to 22, a minimum value of the time interval in a case in which a laser output was the smallest was about 300 μs shown in (b) of FIG. 20. Therefore, it was confirmed that the second detected waveform was detected at least 100 μs after the first detected waveform was detected.

REFERENCE SIGNS LIST

1 . . . AE sensor, 2 . . . workpiece member, 4 . . . measuring instrument (measuring system), 6 . . . adjusting unit, 7 . . . laser source, 42 . . . arithmetic unit (signal acquiring unit, input function calculating unit, evaluating unit), 43 . . . recording unit (storage medium).

The invention claimed is:

1. A laser peening method, comprising:
    generating a shock wave by an ablation with a laser in a liquid to obtain a first peening effect;
    obtaining a shock wave due to collapse of the cavitation bubbles generated by a pressure change that occurs in the liquid to obtain a second peening effect;
    a signal acquiring step of acquiring a detected waveform output during a laser peening processing by an AE sensor that detects an elastic wave generated in a workpiece member;
    an input function calculating step of calculating an input function I(t) by laser irradiation using, when the detected waveform is represented as V(t), an input function by the laser irradiation is represented as I(t), a response function of the AE sensor is represented as S(t), a green function of the workpiece member is represented as G(t), and a convolutional integral is represented as *, a first relational expression $$V(t)=S(t)*G(t)*I(t)$$

and on the basis of the response function S(t) of the AE sensor acquired in advance, the green function G(t) of the workpiece member acquired in advance, and the detected waveform V(t) acquired in the signal acquiring step; and
    an evaluating step of evaluating impact force using the input function I(t) by the laser irradiation.

2. The laser peening method according to claim 1, wherein, in the input function calculating step, the input function I(t) is calculated using at least an AE waveform including a first peak amplitude value, which is an amplitude value of a peak detected first in the detected waveform acquired in the signal acquiring step.

3. The laser peening method according to claim 2, wherein, in the input function calculating step, the input function I(t) is calculated using, in the detected waveform acquired in the signal acquiring step, a second detected waveform detected after a first detected waveform having an amplitude value attenuated from the first peak amplitude value set as a maximum.

4. The laser peening method according to claim 3, wherein the second detected waveform is detected after at least 100 μs from the detection of the first detected waveform.

5. The laser peening method according to claim 1, wherein
    the input function calculating step includes an estimating step of estimating or specifying a function representing attenuation of a peak amplitude value of the detected waveform acquired in the signal acquiring step, and
    the input function I(t) by the laser irradiation is calculated using the function estimated or specified by the estimating step and the peak amplitude value.

6. The laser peening method according to claim 1, wherein the response function S(t) of the AE sensor and the green function G(t) of the workpiece member are acquired by calibration and a simulation performed using a finite element method.

7. The laser peening method according to claim 6, wherein the calibration is performed using data obtained by breaking a lead of a mechanical pencil.

8. The laser peening method according to claim 6, wherein, in the simulation performed using the finite element method, the green function G(t) of the workpiece member is obtained using data concerning a shape and a material of the workpiece member and simulative impact force.

9. The laser peening method according to claim 6, wherein, when a detected waveform for the purpose of calculation is represented as $V_{test}(t)$, an input function for the purpose of calculation by an AE source is represented as $I_{test}(t)$, and the convolutional integral is represented as *, the green function $G(t)$ of the workpiece member is acquired by a simulation using a second relational expression:

$$V_{test}(t)=G(t)*I_{test}(t).$$

10. The laser peening method according to claim 9, wherein
a detected waveform $V_e(t)$ obtained by breaking a lead, the green function $G(t)$ of which is known, is acquired using the AE sensor,
a detected waveform $V_{cal}(t)$ for the purpose of calculation is acquired using an input function $I_{cal}(t)$ in breaking the lead according to a third relational expression:

$$V_{cal}(t)=G(t)*I_{cal}(t)$$

and
the response function $S(t)$ of the AE sensor is calculated using a fourth relational expression:

$$V_e(t)=S(t)*G(t)*I_{cal}(t),$$

the third relational expression, and the green function $G(t)$ obtained by the simulation.

11. A laser peening method, comprising:
generating a shock wave by an ablation with a laser in a liquid to obtain a first peening effect;
obtaining a shock wave due to collapse of the cavitation bubbles generated by a pressure change that occurs in the liquid to obtain a second peening effect;
a signal acquiring step of acquiring a detected waveform output during a laser peening processing by an AE sensor that detects an elastic wave generated in a workpiece member;
an input function calculating step of calculating an input function $I(t)$ by laser irradiation using, when the detected waveform is represented as $V(t)$, an input function by the laser irradiation is represented as $I(t)$, a response function of the AE sensor is represented as $S(t)$, a green function of the workpiece member is represented as $G(t)$, and a convolutional integral is represented as *, a first relational expression $$V(t)=S(t)*G(t)*I(t)$$

and on the basis of the response function $S(t)$ of the AE sensor acquired in advance, the green function $G(t)$ of the workpiece member acquired in advance, and the detected waveform $V(t)$ acquired in the signal acquiring step; and
an evaluating step of evaluating impact force using the input function $I(t)$ by the laser irradiation,
wherein the ablation is caused in the liquid in order to obtain a shock wave due to cavitation bubbles, the liquid is water, a vector of a shock wave due to the ablation is changed by water confining the shock wave due to the ablation, not allowing the shock wave due to the ablation to be dispersed to the outside, and a wavelength of the laser is 532 nm as a second harmonic of 1064 nm such that the laser is not attenuated in the water and the water does not cause ablation.

12. The laser peening method according to claim 11, wherein, in the input function calculating step, the input function $I(t)$ is calculated using at least an AE waveform including a first peak amplitude value, which is an amplitude value of a peak detected first in the detected waveform acquired in the signal acquiring step.

13. The laser peening method according to claim 12, wherein, in the input function calculating step, the input function $I(t)$ is calculated using, in the detected waveform acquired in the signal acquiring step, a second detected waveform detected after a first detected waveform having an amplitude value attenuated from the first peak amplitude value set as a maximum.

14. The laser peening method according to claim 13, wherein the second detected waveform is detected after at least 100 μs from the detection of the first detected waveform.

15. The laser peening method according to claim 11, wherein
the input function calculating step includes an estimating step of estimating or specifying a function representing attenuation of a peak amplitude value of the detected waveform acquired in the signal acquiring step, and
the input function $I(t)$ by the laser irradiation is calculated using the function estimated or specified by the estimating step and the peak amplitude value.

16. The laser peening method according to claim 11, wherein the response function $S(t)$ of the AE sensor and the green function $G(t)$ of the workpiece member are acquired by calibration and a simulation performed using a finite element method.

17. The laser peening method according to claim 16, wherein the calibration is performed using data obtained by breaking a lead of a mechanical pencil.

18. The laser peening method according to claim 16, wherein, in the simulation performed using the finite element method, the green function $G(t)$ of the workpiece member is obtained using data concerning a shape and a material of the workpiece member and simulative impact force.

19. The laser peening method according to claim 16, wherein, when a detected waveform for the purpose of calculation is represented as $V_{test}(t)$, an input function for the purpose of calculation by an AE source is represented as $I_{test}(t)$, and the convolutional integral is represented as *, the green function $G(t)$ of the workpiece member is acquired by a simulation using a second relational expression:

$$V_{test}(t)=G(t)*I_{test}(t).$$

20. The laser peening method according to claim 19, wherein
a detected waveform $V_e(t)$ obtained by breaking a lead, the green function $G(t)$ of which is known, is acquired using the AE sensor,
a detected waveform $V_{cal}(t)$ for the purpose of calculation is acquired using an input function $I_{cal}(t)$ in breaking the lead according to a third relational expression:

$$V_{cal}(t)=G(t)*I_{cal}(t)$$

and
the response function $S(t)$ of the AE sensor is calculated using a fourth relational expression:

$$V_e(t)=S(t)*G(t)*I_{cal}(t),$$

the third relational expression, and the green function $G(t)$ obtained by the simulation.

* * * * *